(12) United States Patent
Hales et al.

(10) Patent No.: US 12,207,829 B2
(45) Date of Patent: Jan. 28, 2025

(54) BONE CUTTING GUIDES

(71) Applicant: CARTIVA, INC., Alpharetta, GA (US)

(72) Inventors: Richard Clay Hales, Alpharetta, GA (US); Guixin Zhang, Atlanta, GA (US)

(73) Assignee: STRYKER CORPORATION, Portage, MI (US)

( * ) Notice: Subject to any disclaimer, the term of this patent is extended or adjusted under 35 U.S.C. 154(b) by 363 days.

(21) Appl. No.: 17/633,754

(22) PCT Filed: Aug. 17, 2020

(86) PCT No.: PCT/US2020/046638
§ 371 (c)(1),
(2) Date: Feb. 8, 2022

(87) PCT Pub. No.: WO2021/050207
PCT Pub. Date: Mar. 18, 2021

(65) Prior Publication Data
US 2022/0323085 A1    Oct. 13, 2022

Related U.S. Application Data

(60) Provisional application No. 62/899,382, filed on Sep. 12, 2019.

(51) Int. Cl.
| | | |
|---|---|---|
| A61B 17/15 | (2006.01) | |
| A61B 17/02 | (2006.01) | |
| A61B 17/17 | (2006.01) | |
| A61B 17/00 | (2006.01) | |

(52) U.S. Cl.
CPC ........ *A61B 17/1775* (2016.11); *A61B 17/025* (2013.01); *A61B 17/15* (2013.01); *A61B 2017/0046* (2013.01)

(58) Field of Classification Search
CPC ........................................ A61B 17/15–17/158
See application file for complete search history.

(56) References Cited

U.S. PATENT DOCUMENTS

| | | | | |
|---|---|---|---|---|
| 6,440,139 | B2 * | 8/2002 | Michelson | A61B 17/1757 606/80 |
| 8,282,645 | B2 * | 10/2012 | Lawrence | A61B 17/15 623/21.19 |
| 11,510,685 | B2 * | 11/2022 | Fallin | A61B 17/151 |
| 2004/0092943 | A1 * | 5/2004 | Buttermann | A61B 17/1757 606/87 |

(Continued)

FOREIGN PATENT DOCUMENTS

| | | |
|---|---|---|
| CA | 3001898 A1 | 4/2017 |
| WO | 2019113394 A1 | 6/2019 |

OTHER PUBLICATIONS

European Partial Search Report issued in connection with corresponding European Patent Application No. 20862932.9, Aug. 7, 2023, 13 pages.

(Continued)

*Primary Examiner* — Zade Coley
(74) *Attorney, Agent, or Firm* — DUANE MORRIS LLP

(57) ABSTRACT

Bone cutting guides and bone cutting guide assemblies are disclosed that are useful for preparing a bone in a joint space, such as those in mid-foot region joints, to prepare the cartilage end of the bone for receiving cartilage repairing implants such as hydrogel implants.

10 Claims, 29 Drawing Sheets

(56) References Cited

U.S. PATENT DOCUMENTS

| | | | | |
|---|---|---|---|---|
| 2008/0015605 A1* | 1/2008 | Collazo | ............... | A61B 17/157 |
| | | | | 606/87 |
| 2010/0331847 A1* | 12/2010 | Wilkinson | ............. | A61B 17/16 |
| | | | | 606/88 |
| 2011/0178524 A1* | 7/2011 | Lawrence | .............. | A61B 17/15 |
| | | | | 606/87 |
| 2014/0194999 A1* | 7/2014 | Orbay | ................ | A61B 17/8095 |
| | | | | 606/85 |
| 2016/0213384 A1* | 7/2016 | Fallin | ................... | A61B 17/151 |
| 2016/0235414 A1* | 8/2016 | Hatch | ................ | A61B 17/1739 |
| 2016/0287268 A1* | 10/2016 | Hughes | ............. | A61B 17/1764 |
| 2017/0079669 A1* | 3/2017 | Bays | ..................... | A61B 17/15 |
| 2019/0336140 A1* | 11/2019 | Dacosta | ............ | A61B 17/1682 |
| 2020/0015874 A1* | 1/2020 | Hartson | ............ | A61B 17/8897 |

OTHER PUBLICATIONS

European Search Report issued in connection with corresponding European Patent Application No. 20862932.9, Nov. 8, 2023, 12 pages.

International Search Report and Written Opinion for PCT International Application No. PCT/US2020/046638 dated Nov. 20, 2020.

* cited by examiner

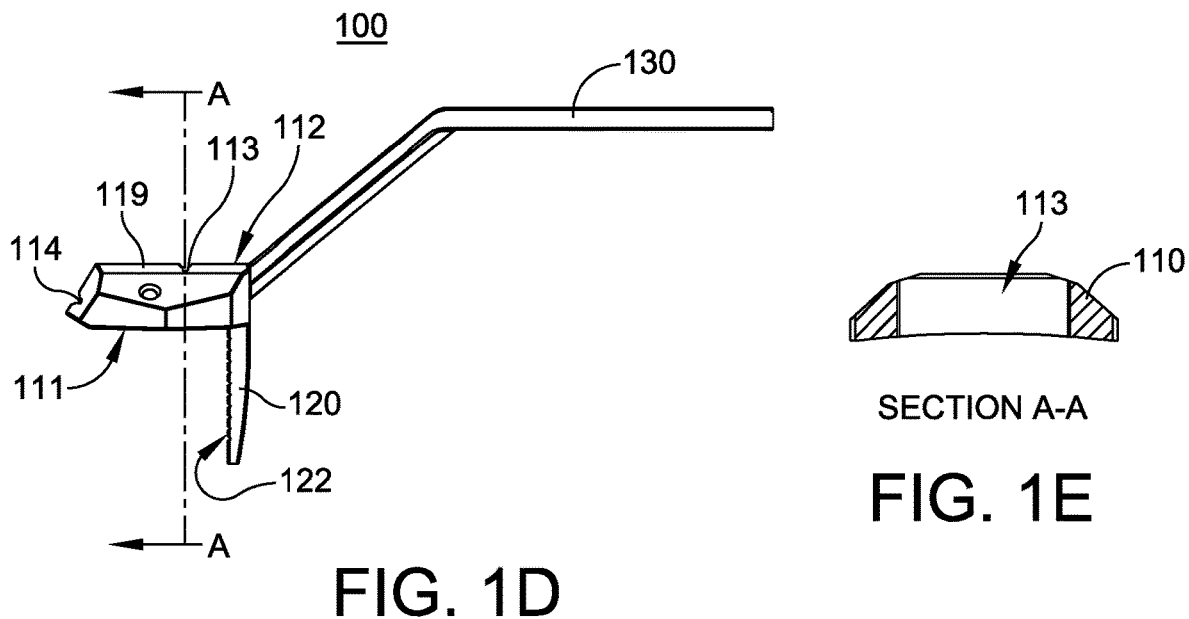
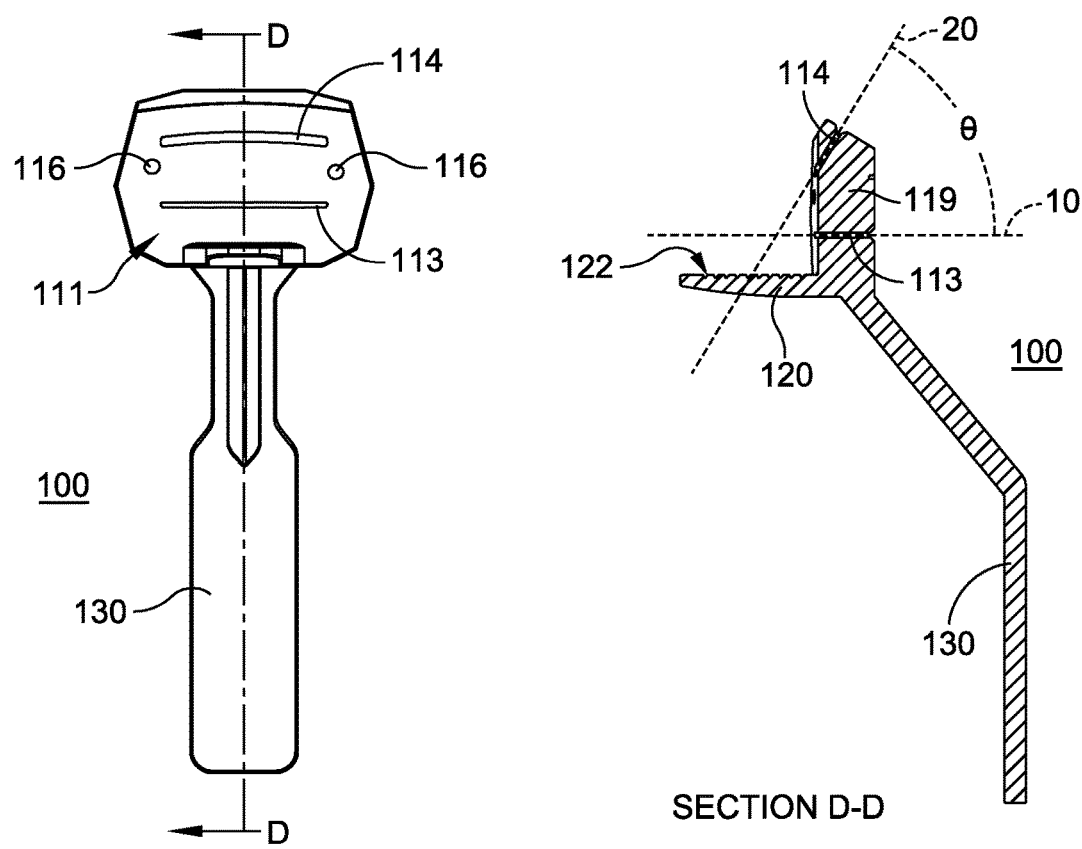

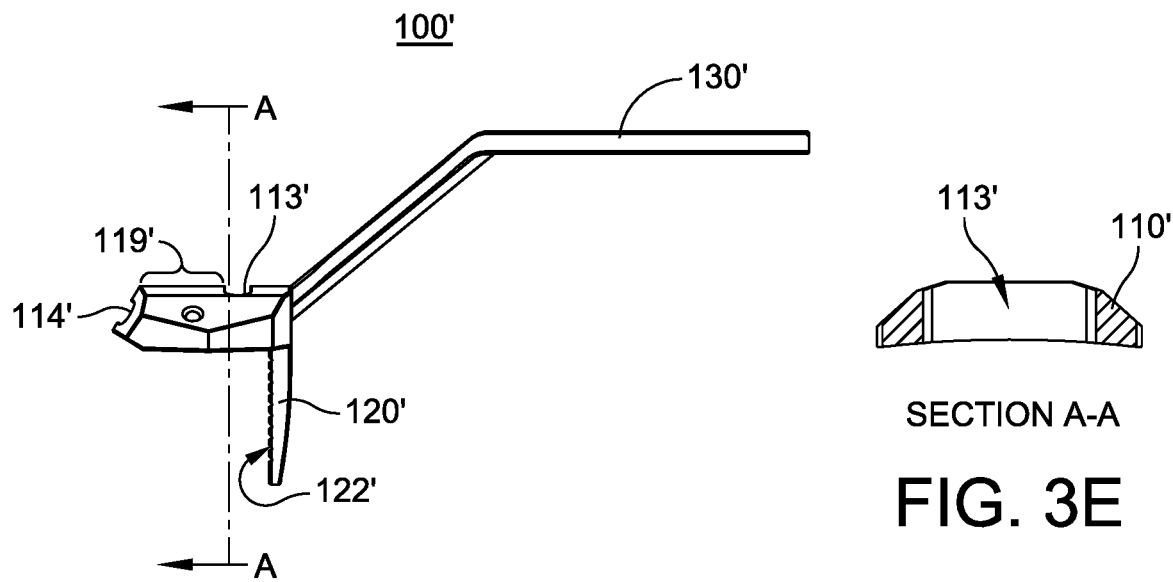
FIG. 3D
FIG. 3E
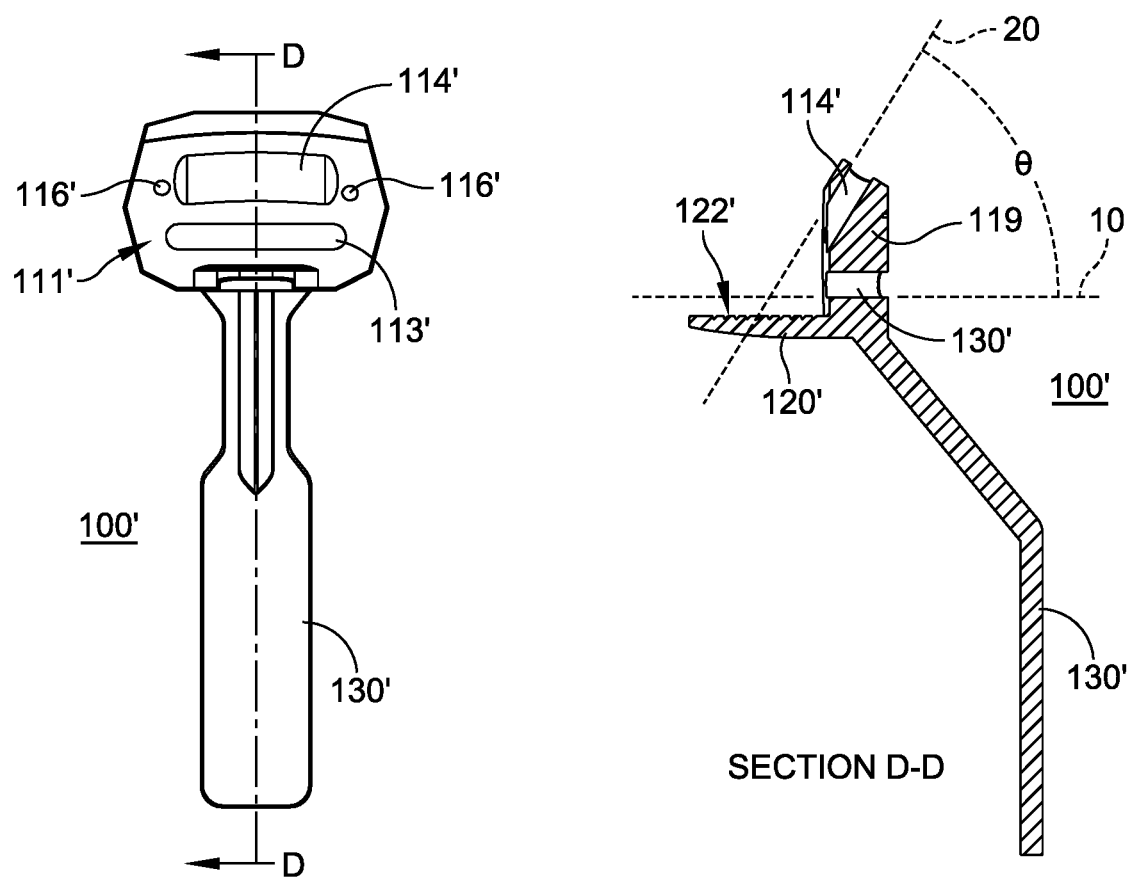
FIG. 3F
FIG. 3G

SECTION A-A

SECTION A-A

SECTION A-A

BONE CUTTING GUIDES

CROSS-REFERENCE TO RELATED APPLICATIONS

This application is a National Stage Application, filed under 35 U.S.C. 371, of International Patent Application No. PCT/US2020/046638, filed on Aug. 17, 2020, which claims the benefit of U.S. Provisional Application Ser. No. 62/899,382, filed on Sep. 12, 2019, entitled "BONE CUTTING GUIDES," the entireties of which are incorporated herein by reference.

FIELD OF DISCLOSURE

The present disclosure relates generally to orthopedic surgical instruments, and more specifically, to bone cutting guide tools for preparing bone surface in a joint space for receiving cartilage surface repairing implants such as hydrogel implants.

BACKGROUND

In order to install a cartilage surface repairing implant in a joint, the distal surface (the cartilage surface) of a bone in the joint needs to be resected with appropriate cuts to prepare the bone surface for receiving the implant. In order to resect the bone surface in the joint with accuracy and proper orientation, an instrument for guiding the cutting tool is desired to aid the surgeon so that such procedure can be performed repeatedly and with accuracy.

SUMMARY

A bone cutting guide is disclosed that comprises a main body comprising a bottom surface, a top surface, and a first and second cutting guide slots extending through the main body, where the bottom surface is a bone contacting surface, where the first and second cutting guide slots are separated by a portion of the main body, where the first cutting guide slot extends through the main body along a first plane and the second cutting guide slot extends through the main body along a second plane, where the first and second planes intersect each other forming an acute angle between the first and second cutting guide slots; and a distractor tab extending from the bottom surface of the main body.

A bone cutting guide assembly is also disclosed. The bone cutting guide assembly comprises a base member comprising a bottom surface, a top surface, and a main opening, where the bottom surface is a bone contacting surface; at least one interchangeable member, where each of the interchangeable member configured to engage the base member one at a time from the top surface of the base member; where each of the at least one interchangeable member comprising at least one cutting guide hole that overlaps with the main opening and extends through the interchangeable member; and a distractor tab extending from the bottom surface of the main body.

The bone cutting guides and bone cutting guide assemblies disclosed herein are useful for preparing a bone in a joint space, such as those in mid-foot region joints, to prepare the cartilage end of the bone for receiving cartilage repairing implants such as hydrogel implants.

BRIEF DESCRIPTION OF THE DRAWINGS

The various embodiments of the inventive subject matter of the present disclosure will be described in more detail in conjunction with the following drawing figures. The structures in the drawing figures are illustrated schematically, and they are not drawn to scale. The drawings figures are not intended to show actual dimensions.

FIG. 1D is a side view of the bone cutting guide of FIG. 1A.

FIG. 1E is a cross-sectional view of the bone cutting guide taken through the section line A-A denoted in FIG. 1D.

FIG. 1F is a bottom view of the bone cutting guide of FIG. 1A.

FIG. 1G is a cross-sectional view of the bone cutting guide of FIG. 1A taken through the section line D-D denoted in FIG. 1F.

FIG. 3D is a side view of the bone cutting guide of FIG. 3A.

FIG. 3E is a cross-sectional view of the bone cutting guide taken through the section line A-A denoted in FIG. 3D.

FIG. 3F is a bottom view of the bone cutting guide of FIG. 3A.

FIG. 3G is a cross-sectional view of the bone cutting guide taken through the section line D-D denoted in FIG. 3F FIGS. 4A-4E are illustrations of the bone cutting guide shown in FIGS. 3A-3G in an example application on a mid-foot joint.

FIGS. 9A-9E are illustrations of the bone cutting guide assembly formed by the combination of the base member shown in FIG. 5A and the interchangeable member shown in FIG. 7A.

DETAILED DESCRIPTION

Figure 1A:
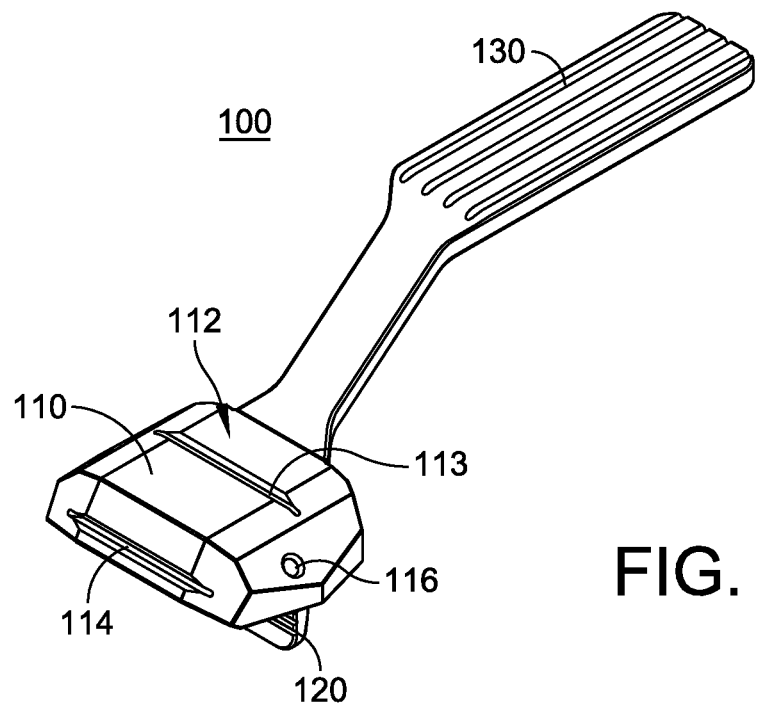
FIG. 1A is an isometric view of a bone cutting guide according to an embodiment of the present disclosure.
Figure 1B:
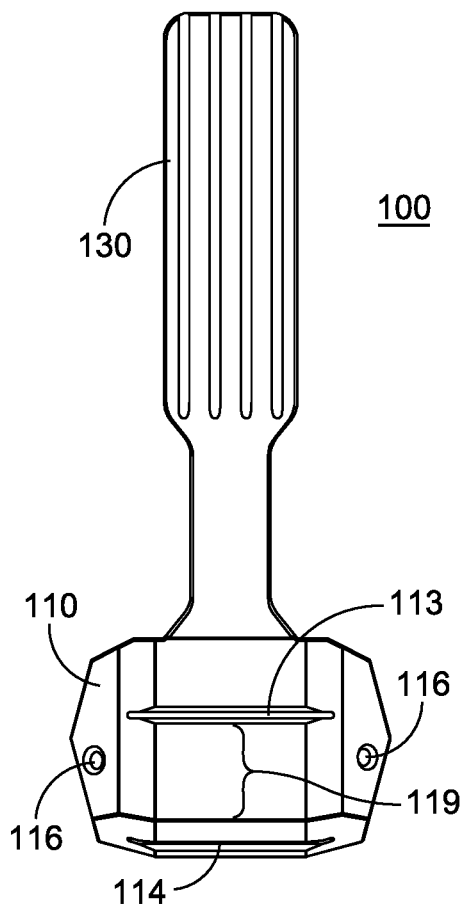
FIG. 1B is a top view of the bone cutting guide of FIG. 1A.

This description of the exemplary embodiments is intended to be read in connection with the accompanying drawings, which are to be considered part of the entire written description. The drawing figures are not necessarily to scale, and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

As used herein, "bone cutting" encompasses sawing of bones as well as removing or grinding bone material using a burr.

[A bone cutting guide for making two angled cuts.]

Referring to FIGS. 1A-1G, according to an embodiment, a bone cutting guide 100 configured for guiding bone cutting saw blades for making two angled cuts into a bone is disclosed. The bone cutting guide 100 comprises a main body 110 and a distractor tab 120. The main body 110 comprises a bottom surface 111, a top surface 112, and a first and second cutting guide slots 113, 114 extending through the main body 110. The bottom surface 111 is a bone contacting surface. The first and second cutting guide slots 113, 114 are separated by a portion 119 of the main body 110.

FIG. 1F is a bottom side view of the bone cutting guide 100. FIG. 1G is a longitudinal cross-section of the bone cutting guide 100 taken through the section line D-D shown in FIG. 1F. Referring to FIG. 1G, the first cutting guide slot 113 extends through the main body 110 along a first plane 10 and the second cutting guide slot 114 extends through the main body 110 along a second plane 20. The planes 10 and 20 are represented in FIG. 1G with dashed lines as in this view, the planes 10 and 20 are oriented orthogonal to the viewing plane. This relationship is shown in FIG. 1G. The first and second planes 10, 20 intersect each other forming an acute angle θ between the first and second cutting guide slots 113, 114. The distractor tab 120 extends from the bottom surface 111 of the main body 110.

In some embodiments of the bone cutting guide 100, the distractor tab 120 can be oriented perpendicular to the bottom surface 111 and comprises a cartilage contacting surface 122 configured for contacting a cartilage surface in the joint when the distractor tab 120 is inserted into a joint to separate the joint. As can be seen in the illustrations, the cartilage contacting surface 122 is oriented to face the side of the bottom surface 111. In some embodiments, the bone contacting surface 111 and the cartilage contacting surface 122 are perpendicular to each other. This configuration is intended for the cartilage contacting surface 122 to be braced against the surface of the cartilage that is being repaired while the bottom surface 111 of the main body 110 contacts the side surface of the associated bone so that the cutting guide slots 113, 114 are positioned for resecting the bone.

The perpendicular relationship between the bone contacting surface 111 and the cartilage contacting surface 122 is a generally preferred arrangement for the bone cutting guide intended for use in mid-foot joint repair procedure involving installation of a cartilage repairing implant on a cuneiform bone. That is because the dorsal (bone surface) and distal (cartilage surface) faces of the cuneiform bones are generally oriented at a right angle relative to one another. A different embodiments of the bone cutting guide 100 can certainly be designed where this angle could be adjusted during surgery to allow for a more exact match. However, this type of embodiment would obviously add more complexity to the procedure and may not significantly impact the final outcome.

Figure 1C:
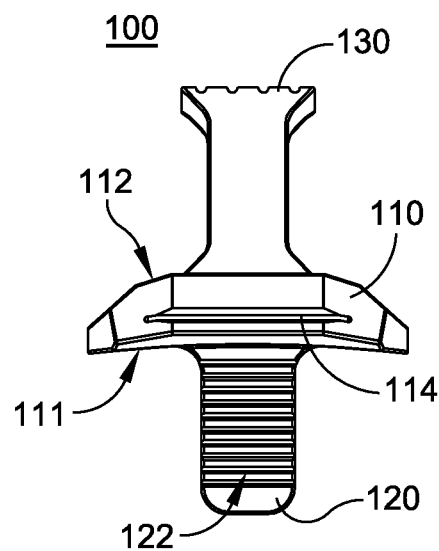
FIG. 1C is a front view of the bone cutting guide of FIG. 1A.

As shown in FIGS. 1C, 1D, and 1G, the cartilage contacting surface 122 can be textured to prevent slippage against the cartilage after the distractor tab 120 has been inserted into the joint and is being held in position during the bone cutting procedure.

In some embodiments, the acute angle θ between the first and second planes 10 and 20 representing the first and second cutting guide slots 113, 114, respectively, is ≥20 degrees and ≤70 degrees. In some embodiments, the acute angle is ≥40 degrees and ≤60 degrees. In some embodiments, the acute angle is ≥50 degrees and ≤60 degrees.

The main body 110 comprises a medial side and a lateral side and further comprises at least two holes 116, one on the lateral side and one on the medial side of the main body, wherein the at least two holes 116 are positioned for receiving guide wires (a.k.a. pins) 50 for securing the main body to a bone. The main body 110 can comprise at least two holes 116 positioned for receiving guide wires 50 (see FIGS. 2A-2C) for securing the main body 110 to the bone to be resected after the distractor tab 120 has been inserted into the joint space and the main body 110 is situated in a desired position.

In all embodiments disclosed herein, the guide wires 50 are angled relative to one another so that the cutting guide's main body 110 is locked against the bone surface once both guide wires are in place. At least one hole 116 is oriented medially and at least one hole is oriented laterally. In a medially oriented hole 116, the top of the hole 116 is closer to the lateral side when the cutting guide is in place on the dorsal side of the foot. In a laterally oriented hole 116, the top of the hole 116 is closer to the medial side when the cutting guide is in place on the dorsal side of the foot. The preferred angle range between the medially oriented hole and the laterally oriented hole is about 50-80 degrees to ensure that all pins are adequately embedded in the bone. This range of angles would also ensure that the pins do not intersect the cutting planes. The angle between the medial and lateral guide wire(s) is as measured in a plane that is parallel to the distractor tab 120. The angle range of 50-80 degrees for the medial and lateral guide wire(s) is equally applicable to all of the embodiments of the cutting guides disclosed.

In some embodiments, each of the first and second cutting guide slots 113, 114 are for guiding a bone cutting saw blade 60 (see FIGS. 2A-2C) and each slot preferably has a width that is selected so that the bone cutting saw blade 60 can be received in the slot and the fit is sufficiently loose to allow the bone cutting saw blade to move in a reciprocating sawing motion during the bone cutting procedure but the fit is also sufficiently snug to keep the bone cutting saw blade in the desired location so that the bone can be resected accurately.

In some embodiments, the first and second cutting guide slots 113 and 114 can be individually provided in separate bone cutting guides. This means that each cutting guide only has one cutting guide slot. Alternatively, the cutting guide can comprise a main body 110 that is configured to receive separate inserts where each insert comprises a cutting guide slot. Thus, in use the main body 110 is first positioned in a joint space and different inserts can be installed into the main body 110 for each cut. This is similar in configuration to the cutting guide assembly 500 described below and illustrated in FIGS. 5A-9D.

The bone cutting guide 100 can further comprise a handle 130 extending from the main body 110. A user can hold the handle 130 to manipulate the bone cutting guide 100. In this illustrated example, the handle 130 is integrally formed with the main body 110. The handle 130 could also be configured to be removable from the main body 110. The removable handle configuration will be discussed in more detail below in connection with FIGS. 10A-10H.

Figure 2A:
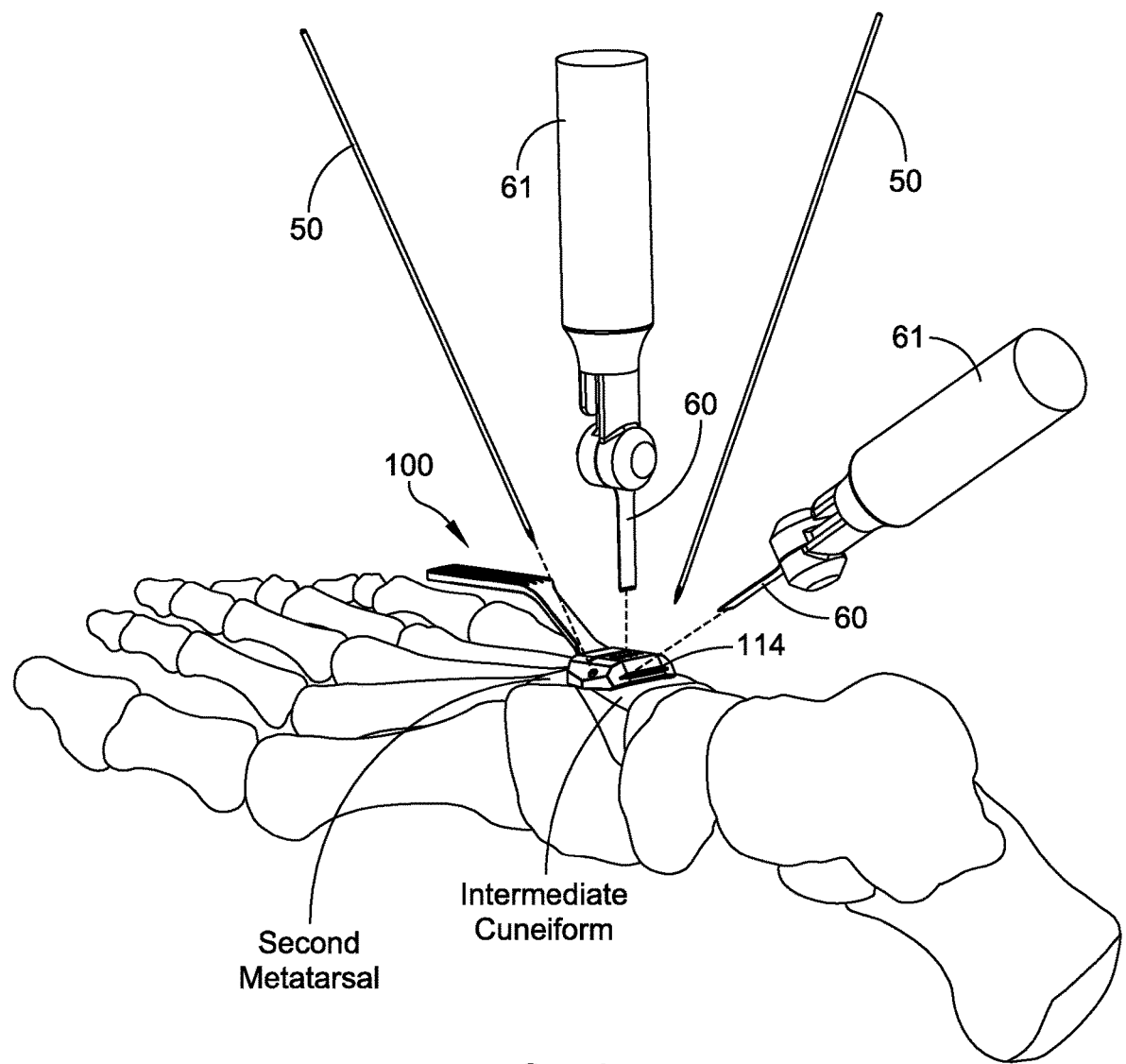
FIGS. 2A-2E are illustrations of the bone cutting guide shown in FIGS. 1A-1G in an example application on a mid-foot joint.
Figure 2B:
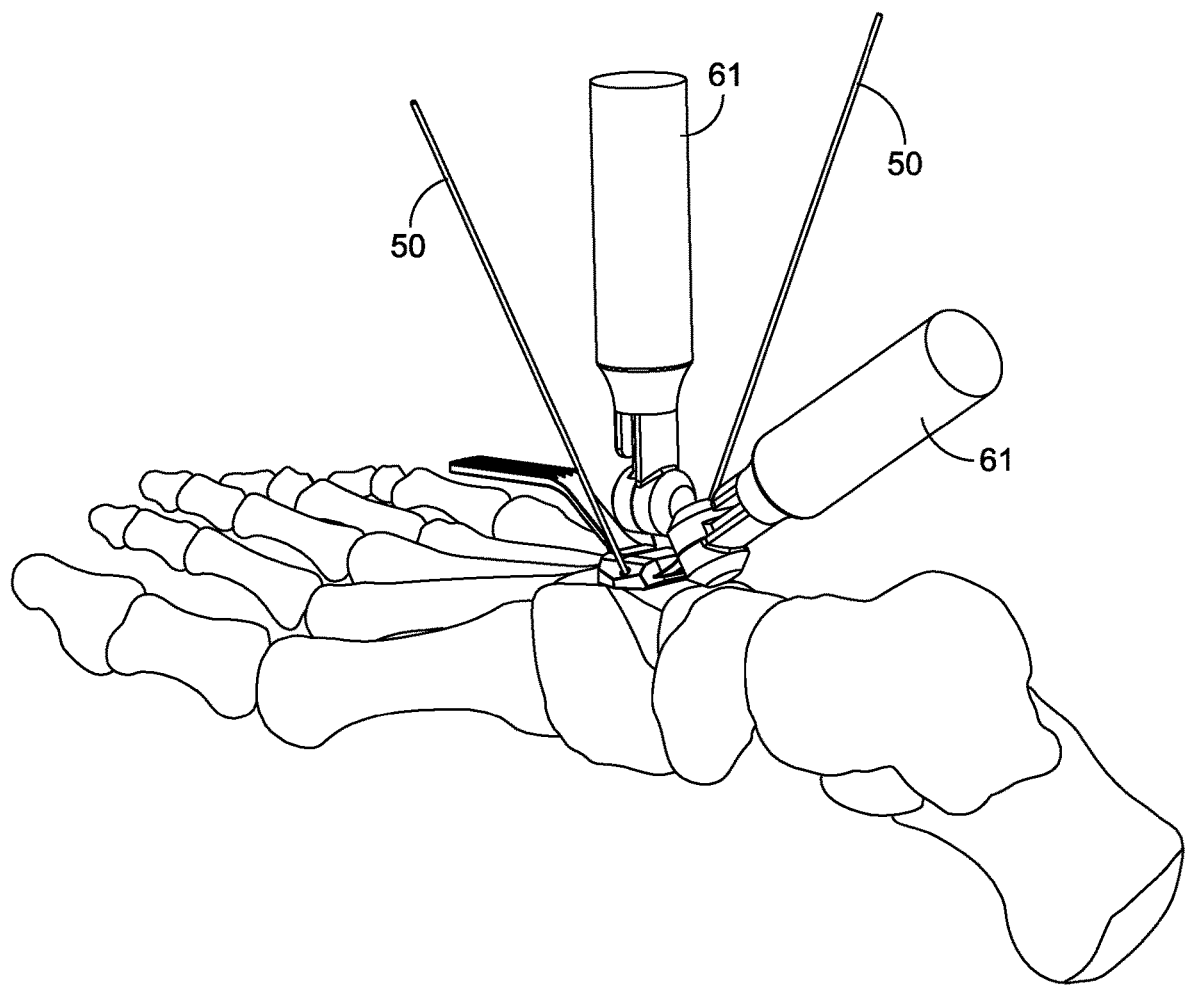
Figure 2C:
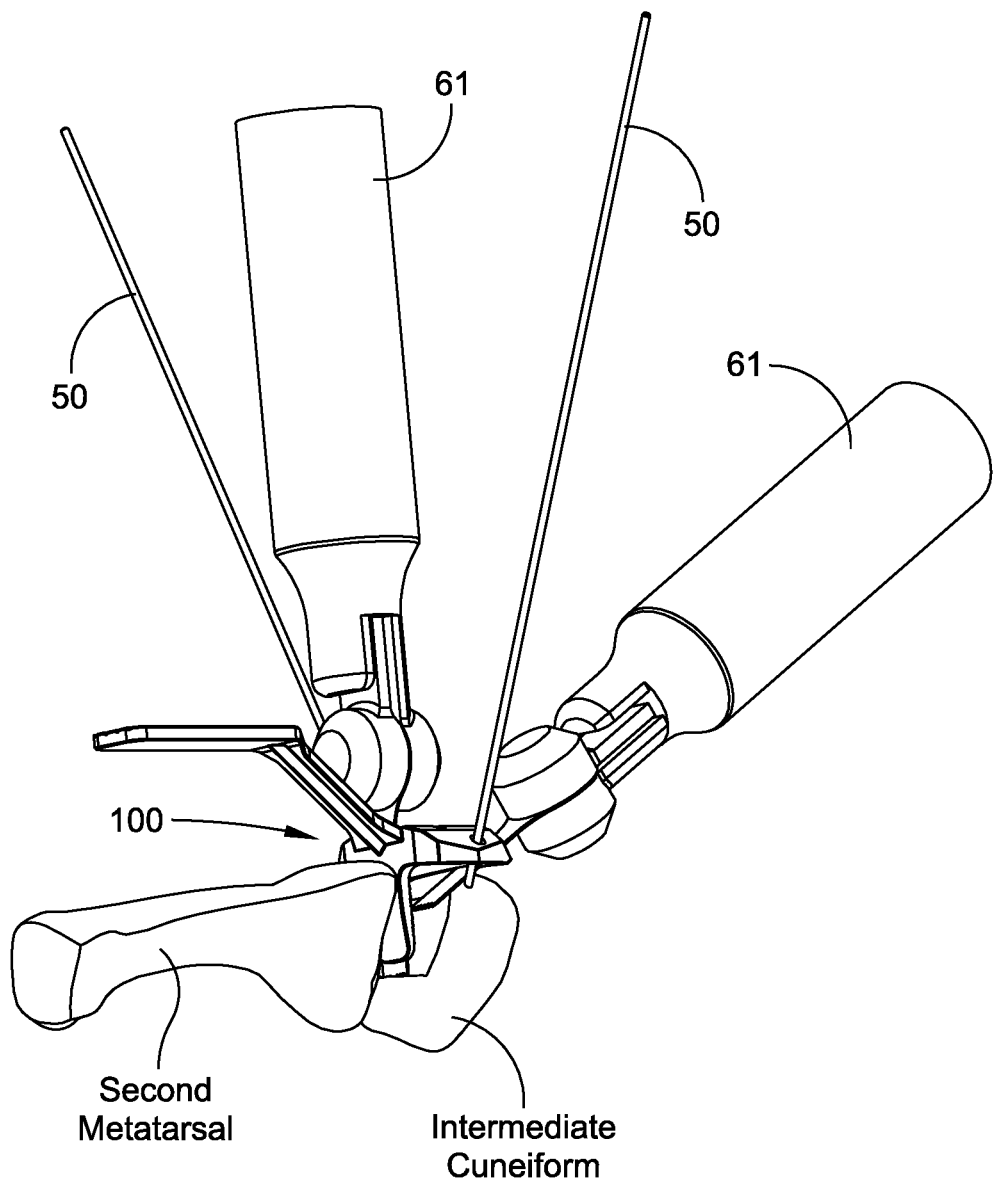

FIGS. 2A-2C are illustrations showing the bone cutting guide 100 being used in an example application in a joint between the intermediate cuneiform bone and the second metatarsal bone. The bone cutting guide 100 can be used in many of the other joints in the mid-foot region. For example, the bone cutting guide 100 can be used in any of the tarsometatarsal (TMT) joints, metatarsophalangeal joints, and any of the joints between the cuneiforms and the respective metatarsal bones. In the illustrated examples shown in FIGS. 2A, 4A, 8A, and 9A, the joint being operated on by the bone cutting guides 100, 100', and bone cutting guide assembly 500 of the present disclosure is the second TMT joint formed between the intermediate cuneiform bone and the second metatarsal bone. One of the cartilage surfaces in the joint is being repaired with a cartilage replacement implant.

FIG. 2A shows the bone cutting guide 100 in position with its distractor tab 120 inserted into the joint space between the intermediate cuneiform bone and the second metatarsal bone. The first and second cutting guide slots 113, 114 are positioned over the intermediate cuneiform bone which is intended to be resected so that its cartilage surface can be repaired. Two guide wires 50 are shown in position oriented to be inserted into the two holes 116 in the main body 110 to secure the main body 110 to the intermediate cuneiform bone before the sawing can begin. Two bone saw blades 60 are shown oriented at angles that match the angles of the two cutting guide slots 113, 114 in ready position to cut into the bone through the cutting guide slots 113, 114. The saw blades 60 are held by the associated handles 61.

FIGS. 2B and 2C show the two guide wires 50 in installed position securing the main body 110 to the intermediate cuneiform bone. Two bone saw blades 60 are shown cutting into the bone in their respective orientations guided by the first and second cutting guide slots 113, 114. Two bone saw blades 60 are shown for illustration purposes and the two cuts guided by the slots 113 and 114 would not necessarily be made simultaneously using two blades at the same time. In actual bone cutting procedure, one saw blade 60 can be used to make the two cuts sequentially.

Figure 2D:
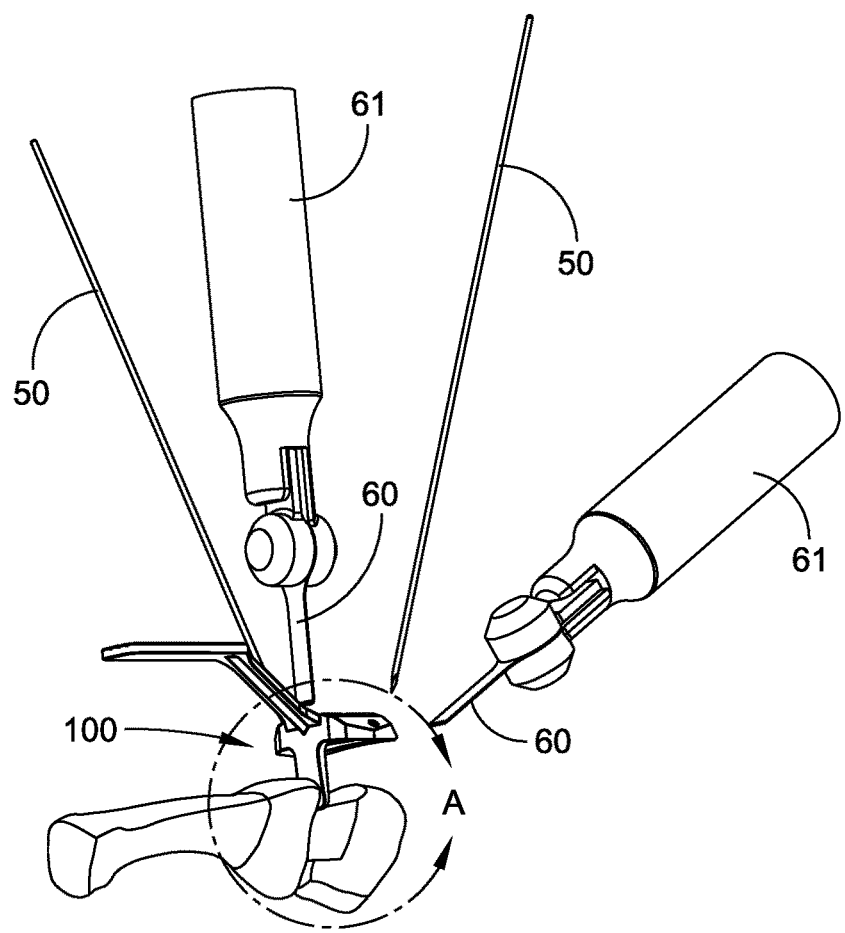
Figure 2E:
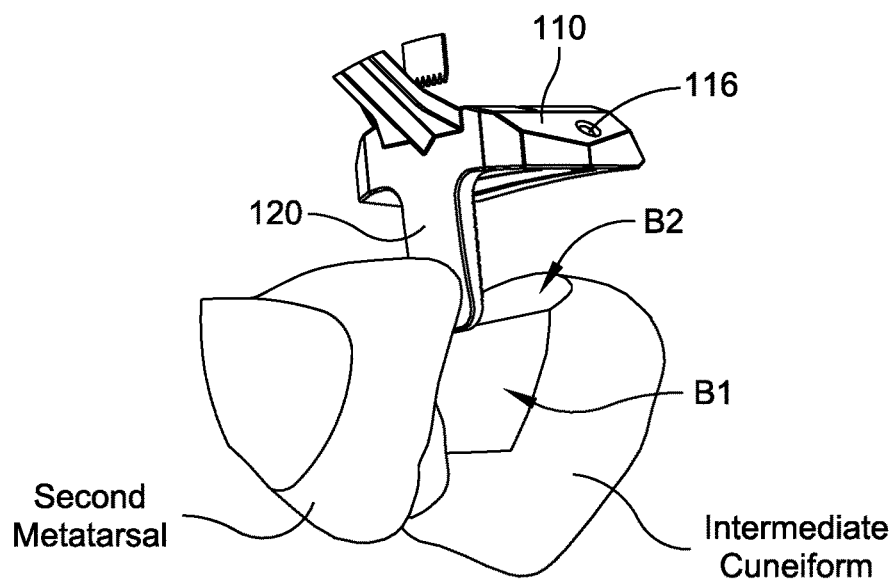

FIG. 2D shows a detailed view of the two bones associated with the joint after the cuts have been made. The bone cutting guide 100, the guide wires 50, and the blades 60 are shown retreated from the joint so that the resected bone surfaces can be seen. FIG. 2E shows a close up view of the region A denoted in FIG. 2D. The two cuts made into the bone (the intermediate cuneiform bone in this example) guided by the cutting guide slots 113, 114 that are oriented at the acute angle θ will result in two resected surfaces B1 and B2. The resected surface B1 represents the surface made by the cut guided by the first cutting guide slot 113. The resected surface B2 represents the surface made by the cut guided by the second cutting guide slot 114. Because the cutting guide slots are oriented at the acute angle θ, the two resected surfaces B1 and B2 will form an obtuse angle that is equal to (180−θ) degrees. [A bone cutting guide for use with a rotating burr.]

Referring to FIGS. 3A-3G, according to another embodiment, a bone cutting guide 100' configured for guiding bone cutting burrs for cutting into a bone in a joint space is disclosed. The bone cutting guide 100' can be used to form two angled bone surfaces to the cartilage end of a bone that forms the joint similar to the bone cutting guide 100. However the bone cutting guide 100' is configured to accommodate a larger (thicker) rotating cutting instrument such as a burr. Alternatively, the bone cutting guide 100' can be used to guide rotating burrs to further condition the surfaces of the resected bone surfaces that were cut using the bone cutting guide 100 shown in FIGS. 1A-1G.

The bone cutting guide 100' comprises a main body 110' and a distractor tab 120'. The main body 110' comprises a bottom surface 111', a top surface 112', and a first and second cutting guide slots 113', 114' extending through the main body 110'. The bottom surface 111' is a bone contacting surface. The first and second cutting guide slots 113', 114' are separated by a portion 119' of the main body 110'.

FIG. 3F is a bottom side view of the bone cutting guide 100'. FIG. 3G is a longitudinal cross-section of the bone cutting guide 100' taken through the section line D-D shown in FIG. 3F. Referring to FIG. 3G, the first cutting guide slot 113' extends through the main body 110' along a first plane 10 and the second cutting guide slot 114' extends through the main body 110' along a second plane 20. The planes 10 and 20 are represented in FIG. 3G with dashed lines as in this view, the planes 10 and 20 are oriented orthogonal to the viewing plane. This relationship is shown in FIG. 3G. The first and second planes 10, 20 intersect each other forming an acute angle θ between the first and second cutting guide slots 113', 114'. The distractor tab 120' extends from the bottom surface 111' of the main body 110'.

In some embodiments of the bone cutting guide 100', the distractor tab 120' can be oriented perpendicular to the bottom surface 111' and comprises a cartilage contacting surface 122' configured for contacting a cartilage surface in the joint when the distractor tab 120' is inserted into a joint to separate the joint. As can be seen in the illustrations, the cartilage contacting surface 122' is oriented to face the side of the bottom surface 111'. In some embodiments, the bone contacting surface 111' and the cartilage contacting surface 122' are perpendicular to each other. This configuration is intended for the cartilage contacting surface 122' to be braced against the surface of the cartilage that is being repaired while the bottom surface 111' of the main body 110' contacts the side surface of the associated bone so that the cutting guide slots 113', 114' are positioned for resecting the bone.

Figure 3A:
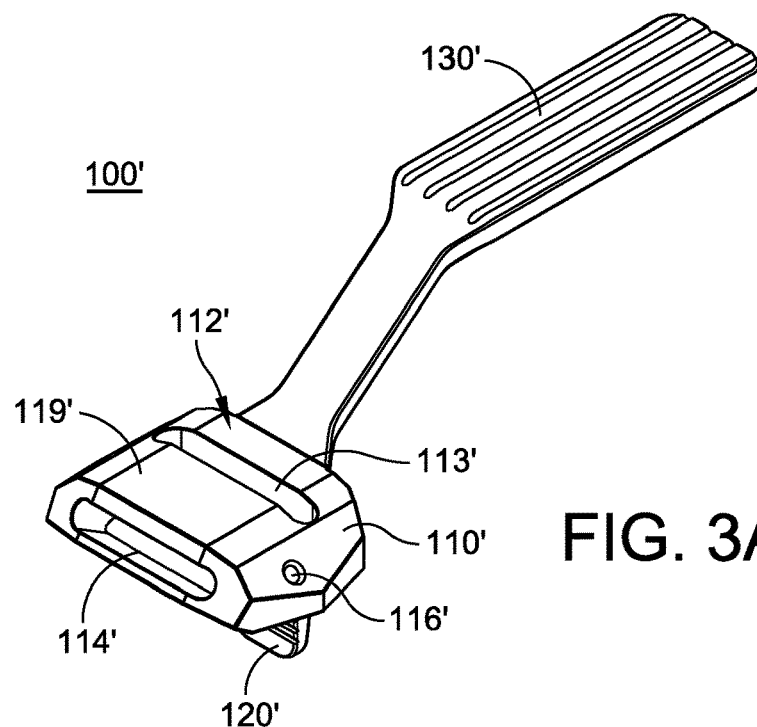
FIG. 3A is an isometric view of a bone cutting guide according to another embodiment of the present disclosure.
Figure 3B:
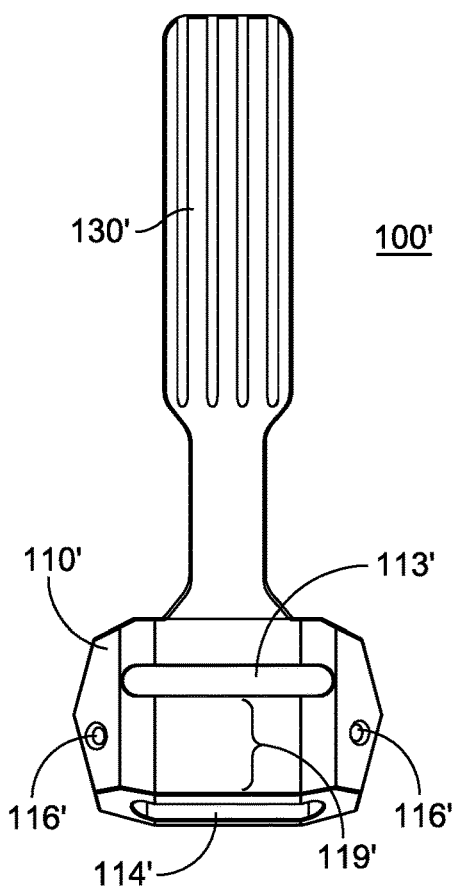
FIG. 3B is a top view of the bone cutting guide of FIG. 3A.
Figure 3C:
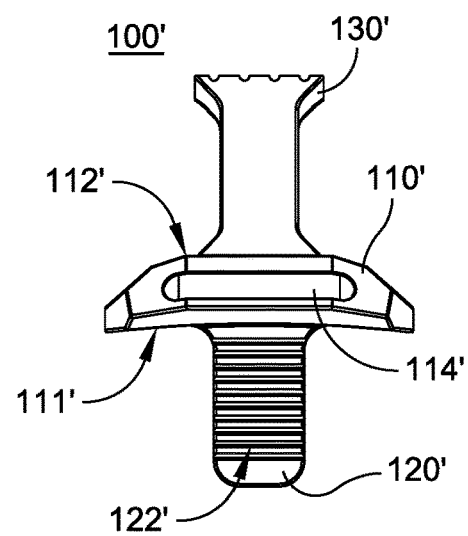
FIG. 3C is a front view of the bone cutting guide of FIG. 3A.

As shown in FIGS. 3C, 3D, and 3G the cartilage contacting surface 122' can be textured to prevent slippage against the cartilage after the distractor tab 120' has been inserted into the joint and is being held in position during the bone cutting procedure.

In some embodiments, the acute angle θ between the first and second planes 10 and 20 representing the first and second cutting guide slots 113', 114', respectively, is ≥20 degrees and ≤70 degrees. In some embodiments, the acute angle is ≥40 degrees and ≤60 degrees. In some embodiments, the acute angle is ≥50 degrees and ≤60 degrees.

The main body 110' can comprise at least two holes 116' positioned for receiving guide wires 50 (see FIGS. 4A-4C) for securing the main body 110' to the bone to be resected after the distractor tab 120 has been inserted into the joint and the main body 110' is situated in a desired position.

In some embodiments, each of the first and second cutting guide slots 113', 114' are for guiding a bone cutting burr 70 (see FIGS. 4A-4C) and each slot preferably has a width that is selected so that the bone cutting burr 70 can be received in the slot and the fit is sufficiently loose to allow the bone cutting burr 70 to move along the guide slot during the bone cutting procedure but the fit is also sufficiently snug to keep the bone cutting burr 70 accurately within a desired location and control the angle and path of the bone cutting burr 70 to accurately shape the bone.

The bone cutting guide 100' can further comprise a handle piece 130' extending from the main body 110'. A user can hold the handle piece 130' to manipulate the bone cutting guide 100'.

Figure 4A:
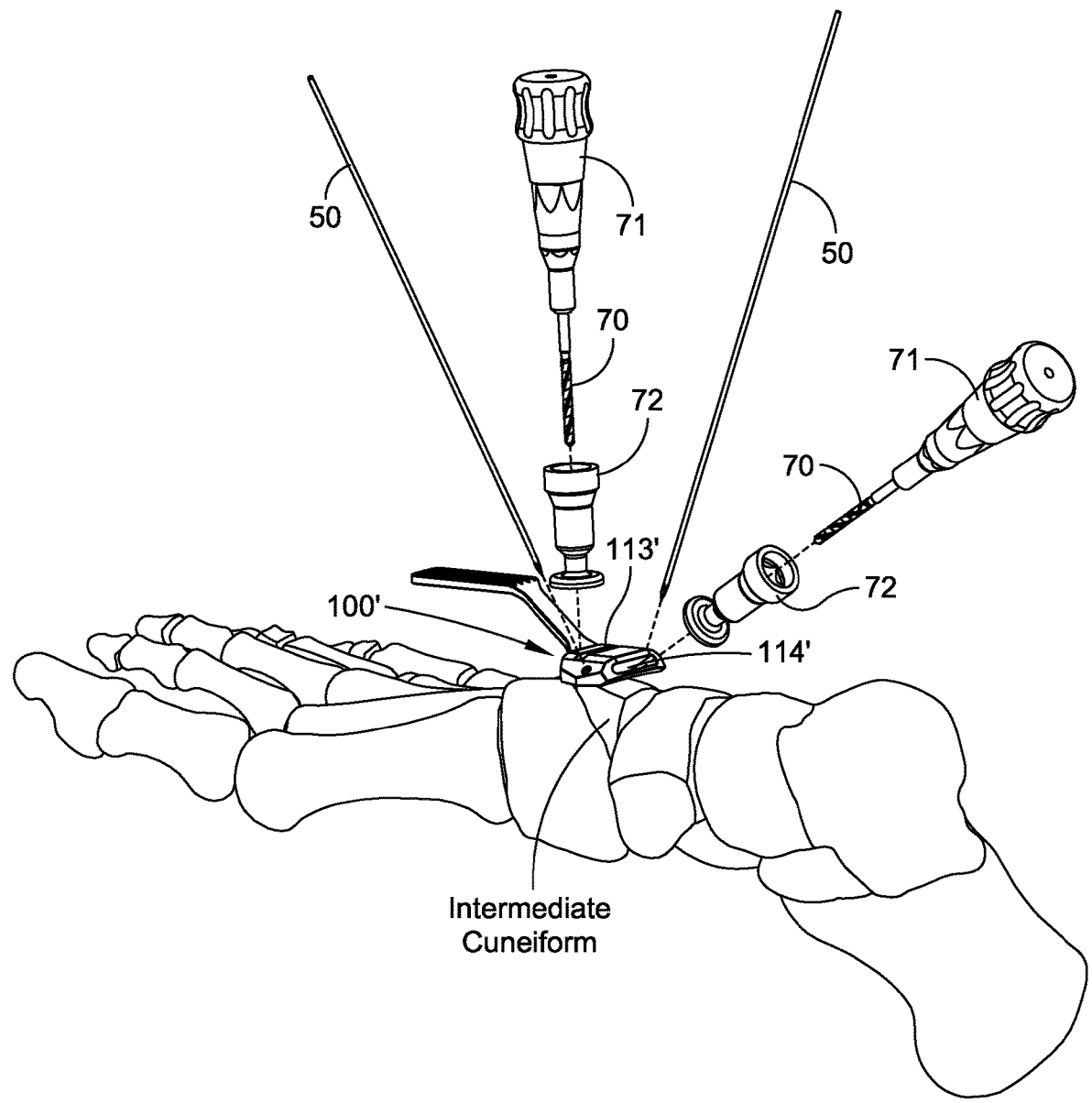
Figure 4B:
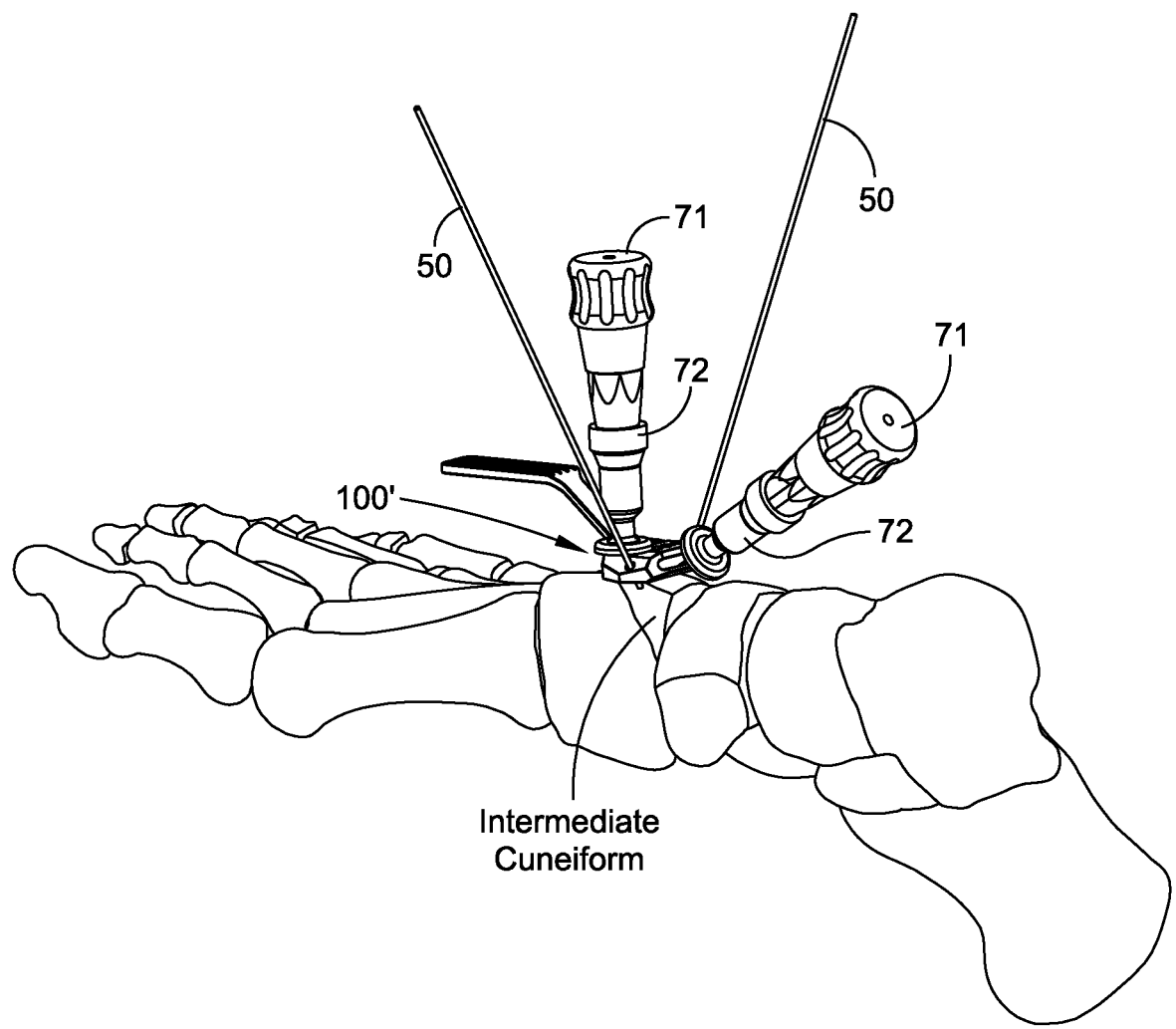
Figure 4C:
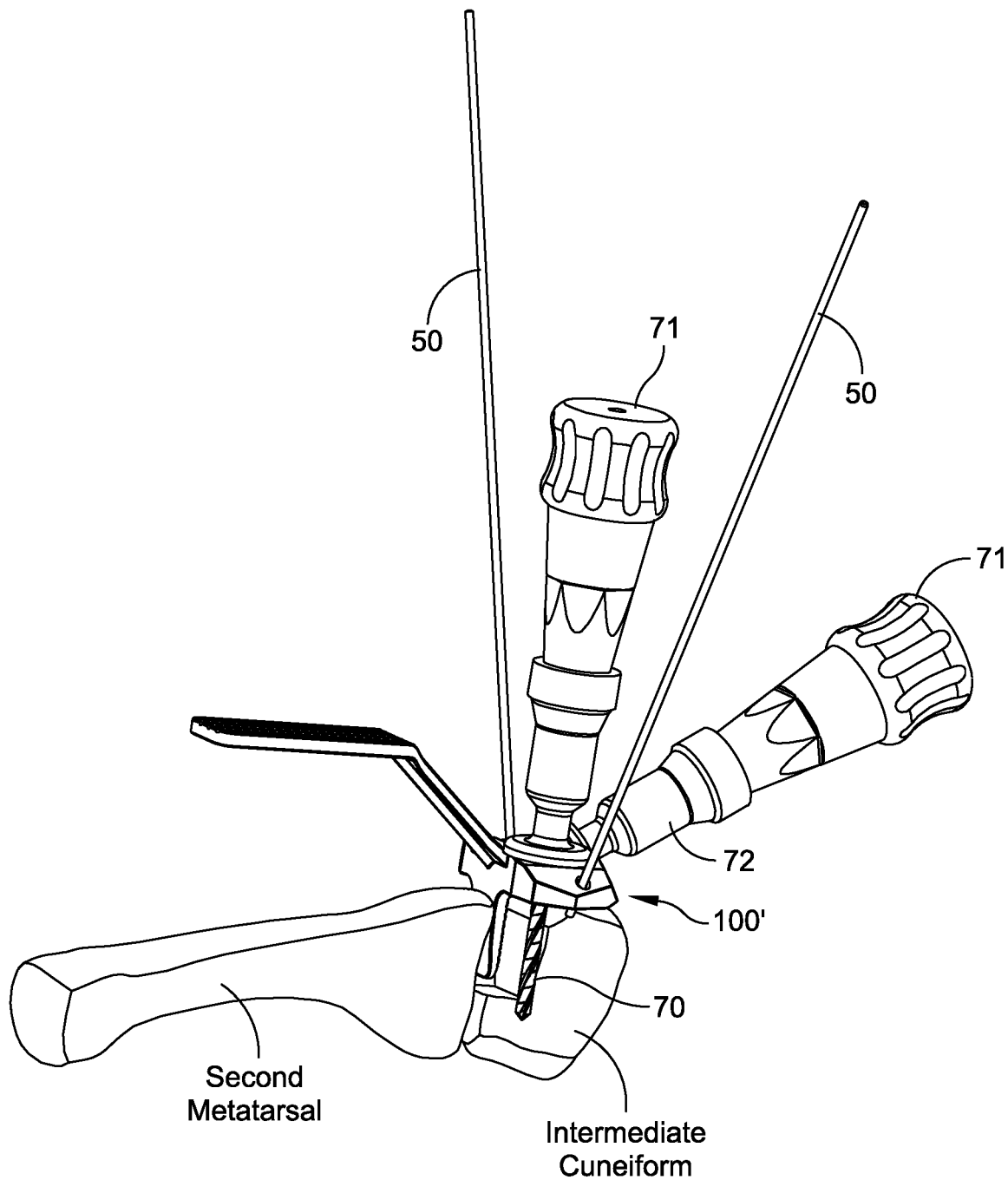

FIGS. 4A-4C are illustrations showing the bone cutting guide 100' being used in an example application in a joint between the intermediate cuneiform bone and the second metatarsal bone. The bone cutting guide 100' can be used in many of the other joints in the mid-foot region. For example, the bone cutting guide 100' can be used in the joint between the intermediate cuneiform bone and the second metatarsal bone, the joint between the lateral cuneiform bone and the second metatarsal bone, any of the TMT joints, and metatarsophalangeal joints, etc. where one of the cartilage surfaces in the joint is being repaired with a cartilage replacement implant.

FIG. 4A shows the bone cutting guide 100' in position with its distractor tab 120' inserted into the joint space between the intermediate cuneiform bone and the second metatarsal bone. The first and second cutting guide slots 113', 114' are positioned over the intermediate cuneiform bone which is intended to be resected so that its cartilage surface can be repaired. Two guide wires 50 are shown in position oriented to be inserted into the two holes 116' in the main body 110' to secure the main body 110' to the intermediate cuneiform bone before the sawing can begin. Two bone cutting burrs 70 are shown oriented at angles that match the angles of the two cutting guide slots 113', 114' in ready position to cut into the bone through the cutting guide slots 113', 114'. The bone cutting burrs 70 are held by the associated driver handles 71. The bone cutting burrs 70 also have associated sleeves 72.

FIGS. 4B and 4C show the two guide wires 50 in installed position securing the main body 110 to the intermediate cuneiform bone. Two bone cutting burrs 70 are shown cutting into the bone in their respective orientations guided by the first and second cutting guide slots 113', 114'. Two bone cutting burrs 70 are shown for illustration purposes and the two cuts guided by the slots 113' and 114' would not necessarily be made simultaneously using two cutting burrs at the same time. In actual bone cutting procedure, one bone cutting burr 70 can be used to make the two cuts sequentially.

Figure 4D:
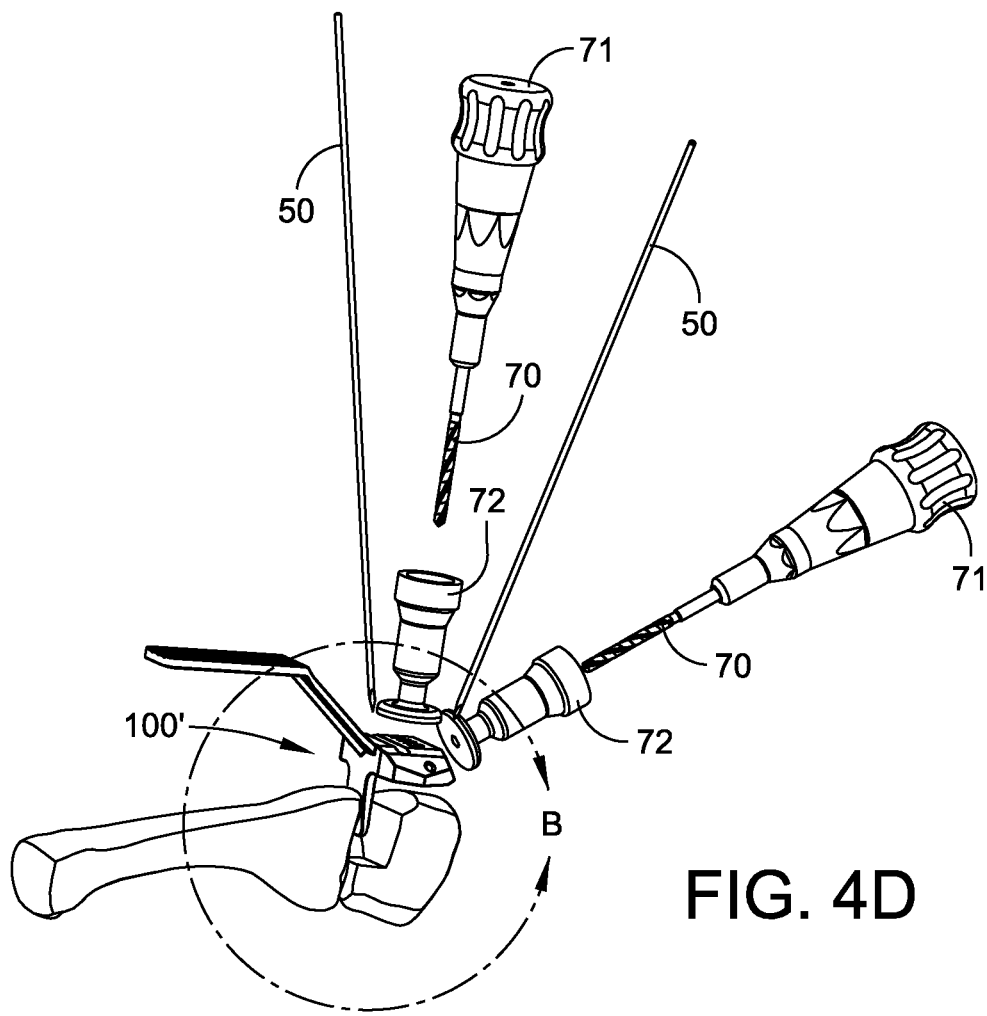
Figure 4E:
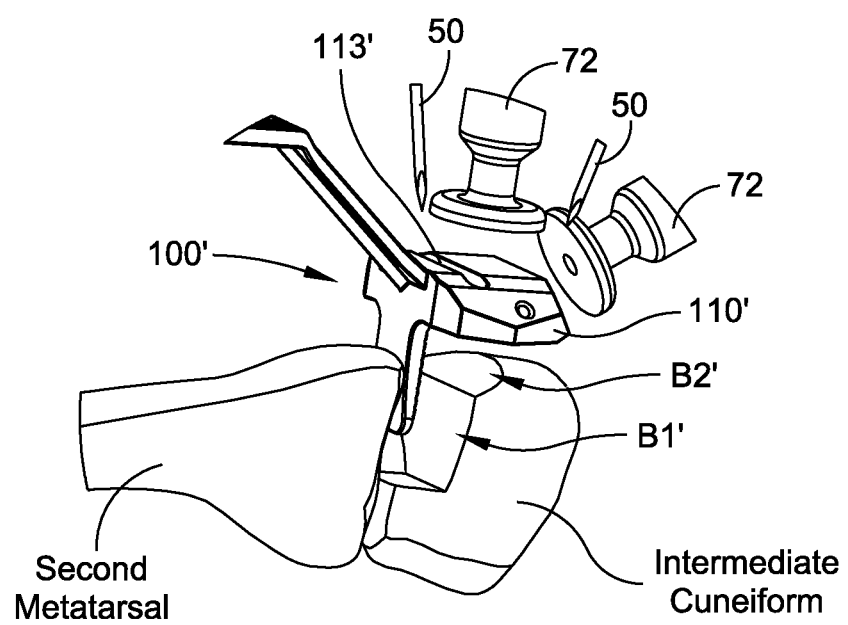
Figure 5A:
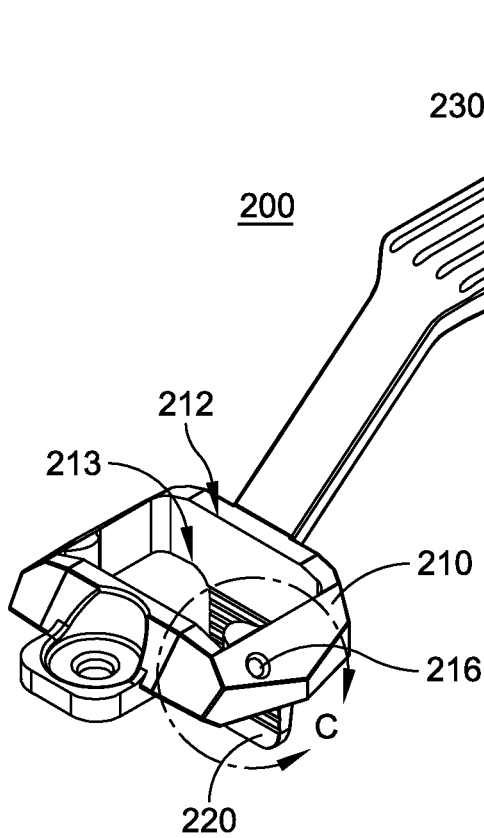
FIG. 5A is an isometric view of a base member of a bone cutting guide assembly according to another embodiment of the present disclosure.
Figure 5B:
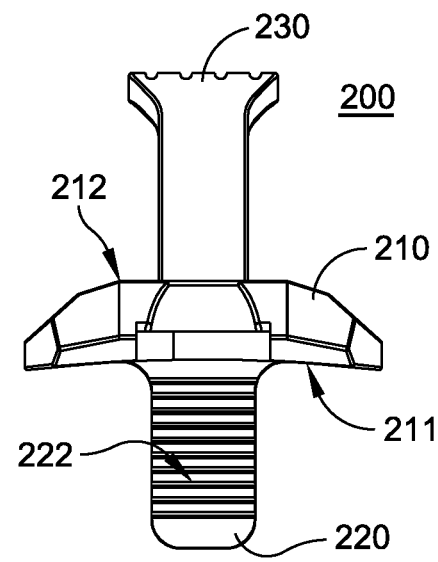
FIG. 5B is a front view of the base member shown in FIG. 5A.
Figure 5C:
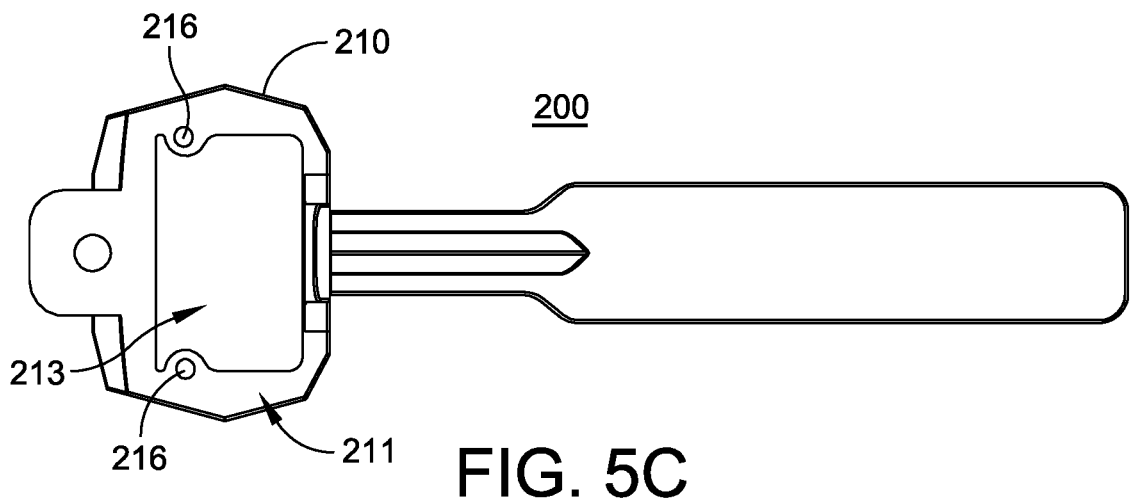
FIG. 5C is a bottom view of the base member shown in FIG. 5A.
Figure 5D:
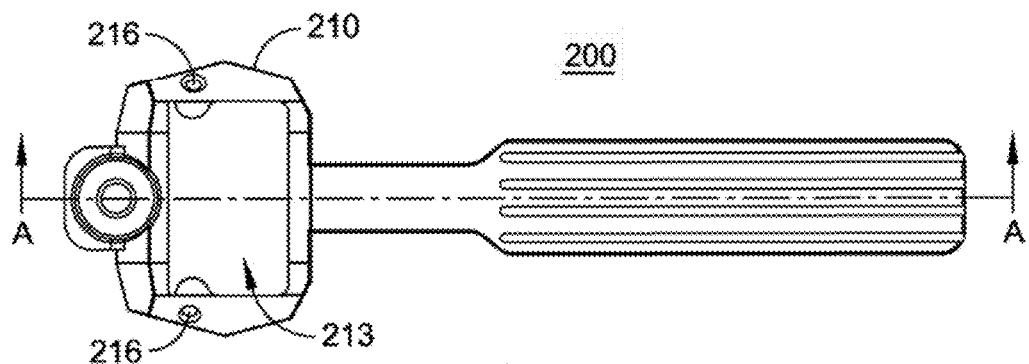
FIG. 5D is a top view of the base member shown in FIG. 5A.
Figure 5E:
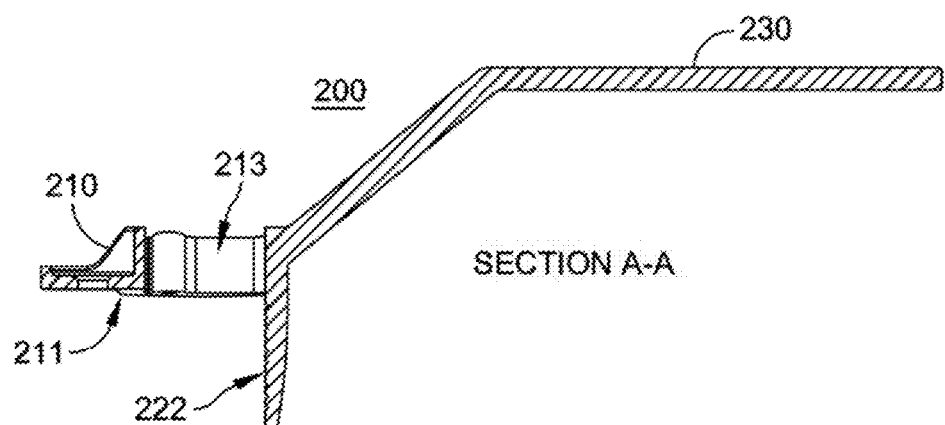
FIG. 5E is a cross-sectional view of the base member taken through the section line A-A denoted in FIG. 5D.
Figure 5F:
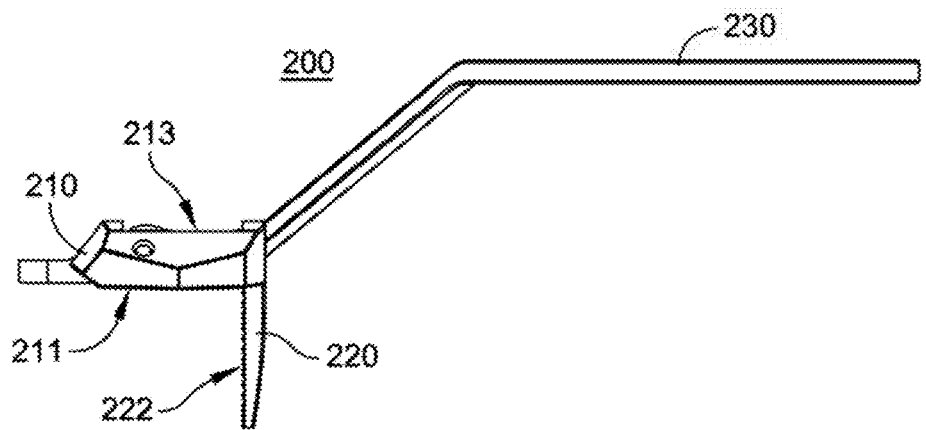
FIG. 5F is a side view of the base member shown in FIG. 5A.

FIG. 4D shows a detailed view of the two bones associated with the joint after the cuts have been made. The bone cutting guide 100', the guide wires 50, and the cutting burrs 70 are shown retreated from the joint so that the resected bone surfaces can be seen. FIG. 4E shows a close up view of the region B denoted in FIG. 4D. The two ground surfaces in the bone (the intermediate cuneiform bone in this example) guided by the cutting guide slots 113', 114' that are oriented at the acute angle θ will result in two conditioned surfaces B1' and B2'. The first conditioned surface B1' represents the surface made by the cut guided by the first cutting guide slot 113'. The second conditioned surface B2' represents the surface made by the cut guided by the second cutting guide slot 114'. Because the cutting guide slots are oriented at the acute angle θ, the two conditioned surfaces B1' and B2' will form an obtuse angle that is equal to (180−θ) degrees.

[A cutting guide assembly for making a flat cut or a half cylinder cut. A base member and an interchangeable member forms the assembly.]

In some embodiments, a bone cutting guide assembly 500 (see FIGS. 8A-9D) for use in resecting a cartilage surface in a joint to prepare the cartilage surface for receiving an implant is disclosed. The joint can be any of the TMT joints, metatarsophalangeal joints, and any of the joints between the cuneiforms and the navicular bone, etc. Referring to FIGS. 5A-7F, the bone cutting guide assembly 500 comprises a base member 200 (see FIGS. 5A-5F) and at least one interchangeable member 300 (see FIGS. 6A-6F) and 400 (see FIGS. 7A-7F). The base member 200 comprises main body 210 and a distractor tab 220. The base member 200 comprises a bottom surface 211, a top surface 212, and a main opening 213. The bottom surface 211 is a bone contacting surface. Each of the at least one interchangeable member 300, 400 is configured to engage the base member 200 one at a time from the top surface of the base member 200.

The distractor tab 220 extends from the bottom surface 211 of the main body 210 of the base member 200. The distractor tab 220 is oriented perpendicular to the bottom surface and comprises a cartilage contacting surface 222 configured for contacting a cartilage surface in the joint. The cartilage contacting surface 222 can be textured to prevent slippage against the cartilage. In the example shown in FIG. 5B, the cartilage contacting surface 222 is textured with a plurality of parallel grooves or ridges.

In the illustrated example, the bone contacting surface 211 of the main body 210 and the cartilage contacting surface 222 are perpendicular to each other. The main body 210 further comprises at least two holes 216 positioned for receiving guide wires 50 for securing the main body 210 to a bone.

FIGS. 6A-6F illustrate an example of an interchangeable member 300 configured to engage the base member 200 to form a bone cutting guide assembly 500 according to an embodiment. The interchangeable member 300 comprises a main body 310 that comprises at least one cutting guide hole 313 that extends through the main body 310. The cutting guide hole 313 overlaps with the main opening 213 when the interchangeable member 300 is engaged to the base member 200.

The cutting guide hole 313 has a width sufficient for receiving and guiding a bone cutting burr 70 (see FIGS. 8A-8D). The main body 310 comprises a first upper surface and a wall 315 that defines the cutting guide hole 313. The wall 315 extends upward from the first upper surface to a predetermined height. As will be discussed below, the cutting guide hole 313 receives a bone cutting burr 70 and the wall 315 interferes with the bone cutting burr's sleeve 72 and stops the bone cutting burr 70 from extending beyond a desired depth into the bone. Therefore, several interchangeable members 300 can be provided with each one having a different height for the wall 315 to provide the orthopedic surgeon the ability to select the proper height.

Figure 6A:
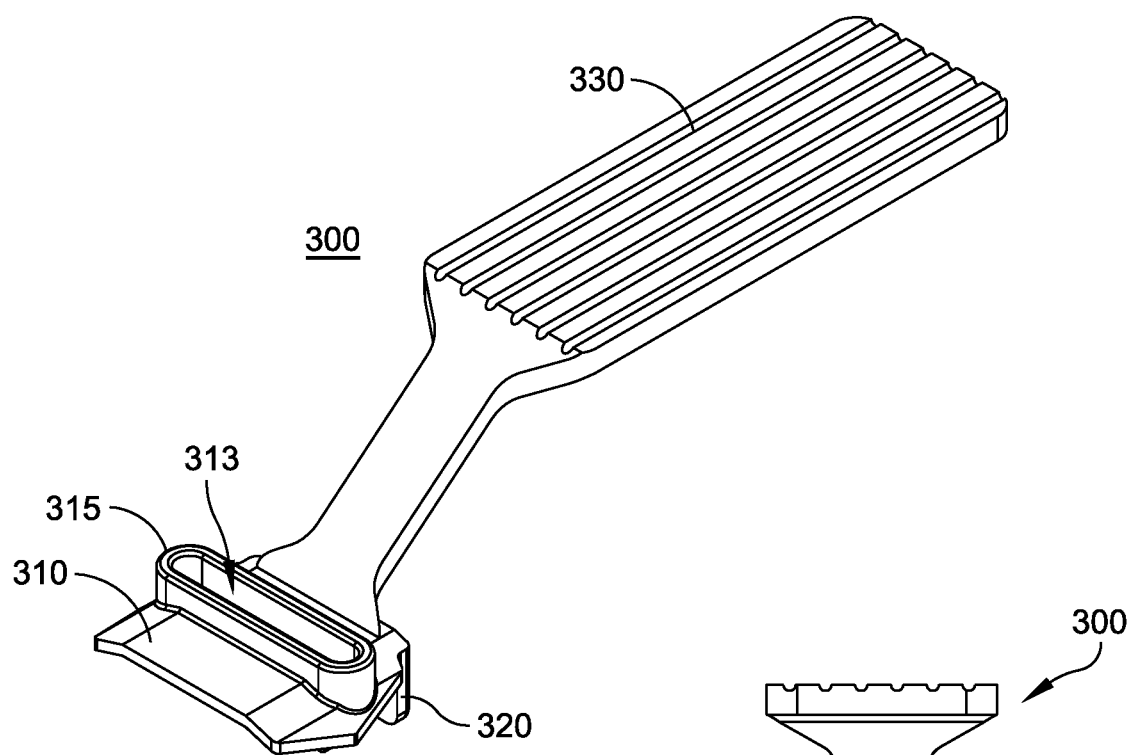
FIG. 6A is an isometric view of an interchangeable member according to an embodiment of the present disclosure.
Figure 6B:
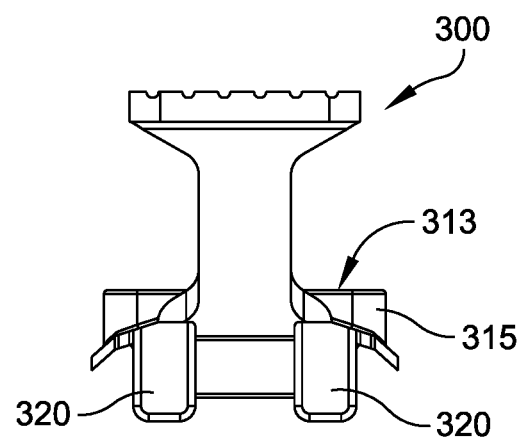
FIG. 6B is a rear view of the interchangeable member shown in FIG. 6A.
Figure 6C:
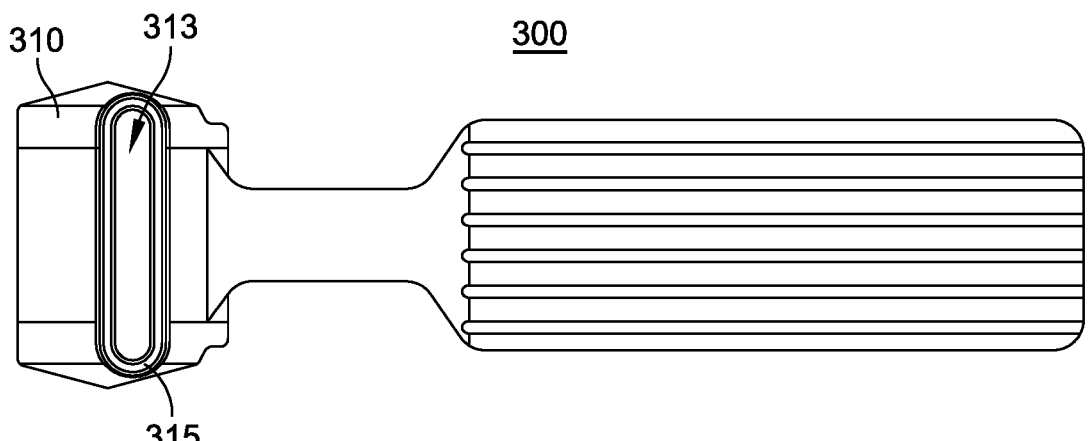
FIG. 6C is a top view of the interchangeable member shown in FIG. 6A.
Figure 6D:
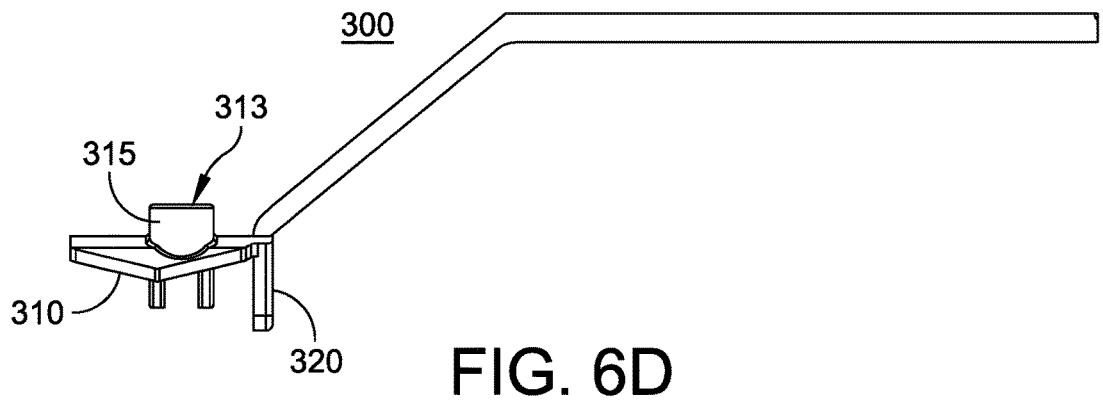
FIG. 6D is a side view of the interchangeable member shown in FIG. 6A.
Figure 6E:
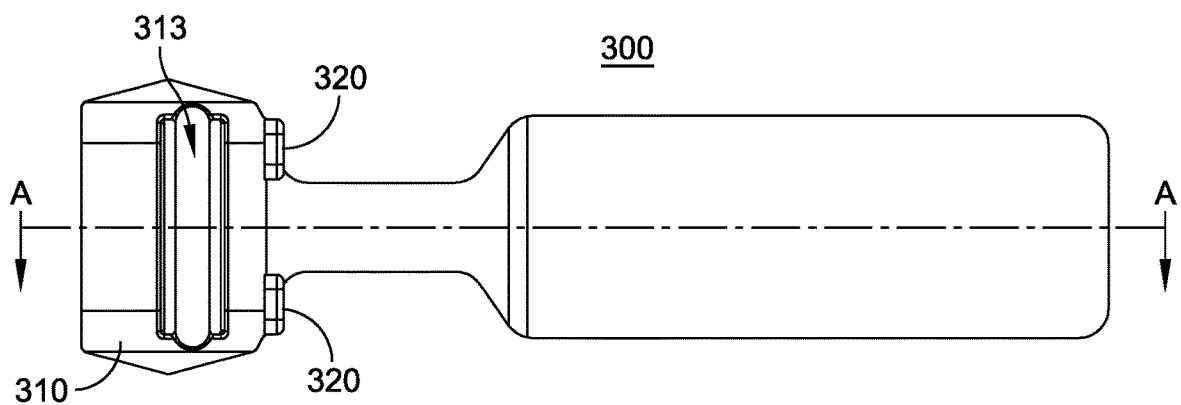
FIG. 6E is a bottom view of the interchangeable member shown in FIG. 6A.
Figure 6F:
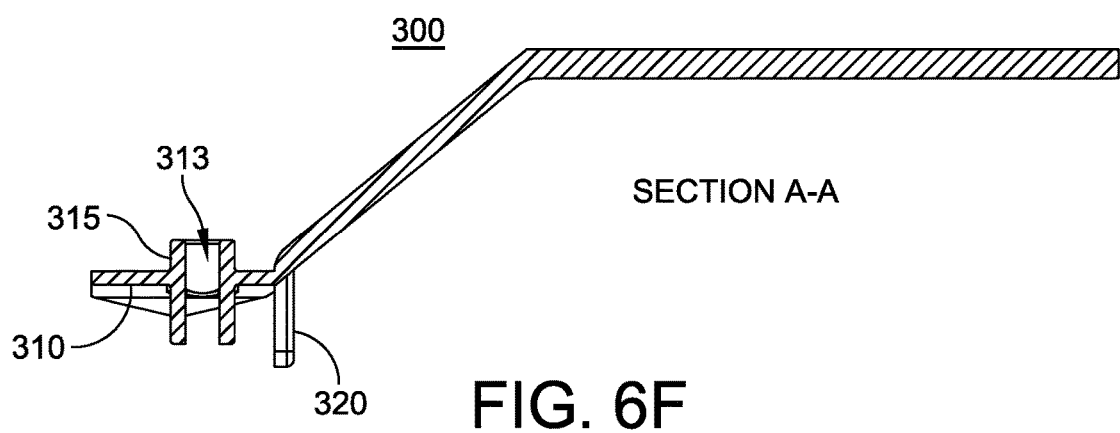
FIG. 6F is a cross-sectional view of the interchangeable member taken through the section line A-A shown in FIG. 6E.

As shown in FIGS. 6A and 6C, the cutting guide hole 313 has a straight elongated shape for forming a straight cut into the bone to form a flat resected bone surface.

Figure 8A:
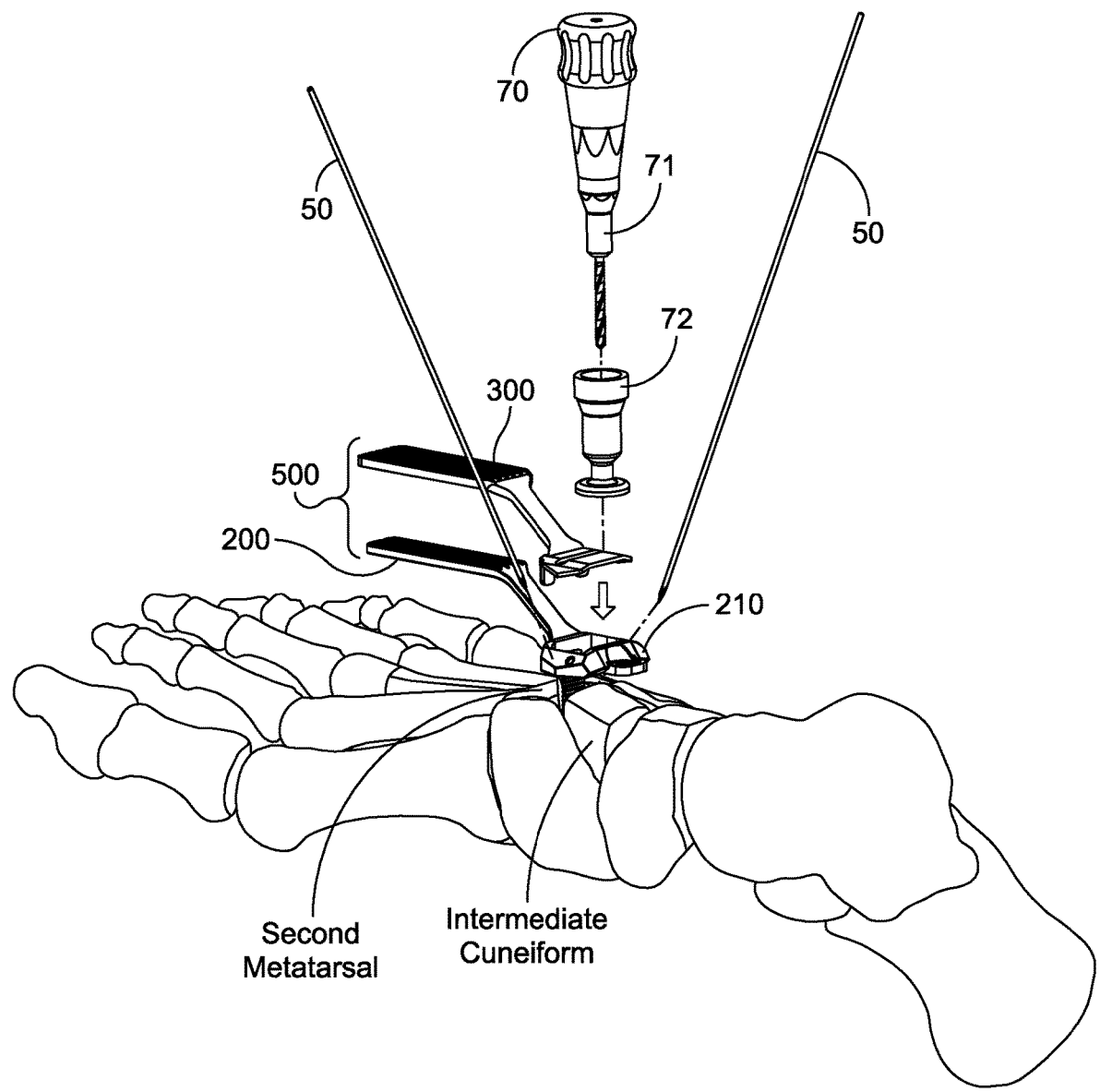
FIGS. 8A-8E are illustrations of the bone cutting guide assembly formed by the combination of the base member shown in FIG. 5A and the interchangeable member shown in FIG. 6A.

As shown in FIG. 8A, the interchangeable member 300 is assembled with the base member 200 to form a bone cutting guide assembly 500 by engaging the base member 200 from the top surface side of the base member 200. As shown in FIG. 6B, the main body 310 of the interchangeable member 300 can comprise two alignment tabs 320 for assisting the engagement of the interchangeable member 300 to the base member 200.

FIGS. 7A-7F illustrate an example of another interchangeable member 400 configured to engage the base member 200 to form a bone cutting guide assembly 500 according to an embodiment. The interchangeable member 400 comprises a main body 410 that comprises at least one cutting guide hole 413 that extends through the main body 410. The cutting guide hole 413 overlaps with the main opening 213 when the interchangeable member 400 is engaged to the base member 200.

The cutting guide hole 413 has a width sufficient for receiving and guiding a bone cutting burr 70 (see FIGS. 8A-8D). The main body 410 comprises a first upper surface and a wall 415 that defines the cutting guide hole 413. The wall 415 extends upward from the first upper surface to a predetermined height. As will be discussed below, the cutting guide hole 413 receives a bone cutting burr 70 and the wall 415 interferes with the bone cutting burr's sleeve 72 and stops the bone cutting burr 70 from extending beyond a desired depth into the bone. Therefore, several interchangeable members 400 can be provided with each one having a different height for the wall 315 to provide the orthopedic surgeon the ability to select the proper height.

Figure 7A:
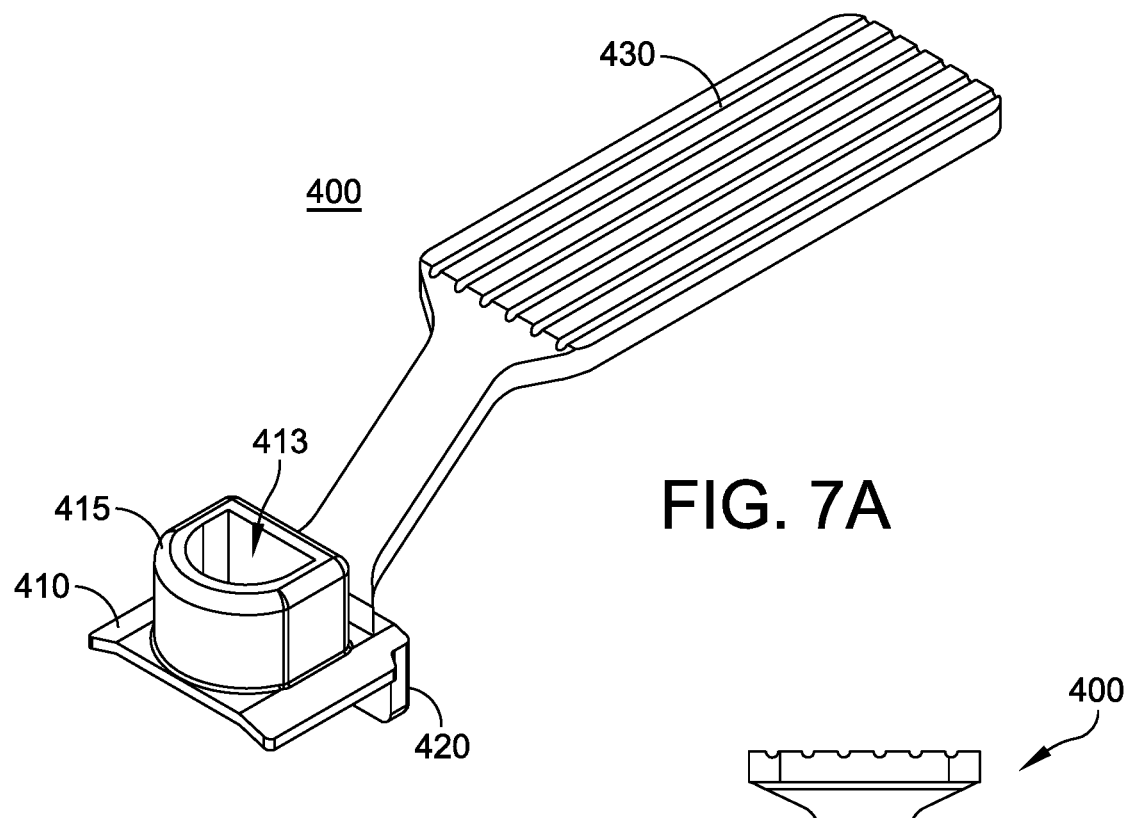
FIG. 7A is an isometric view of another interchangeable member according to an embodiment of the present disclosure.
Figure 7B:
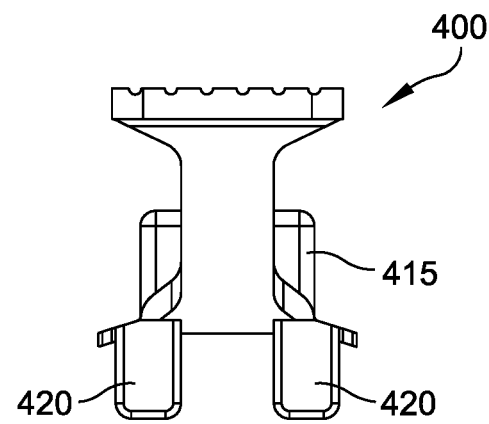
FIG. 7B is a rear view of the interchangeable member shown in FIG. 7A.
Figure 7C:
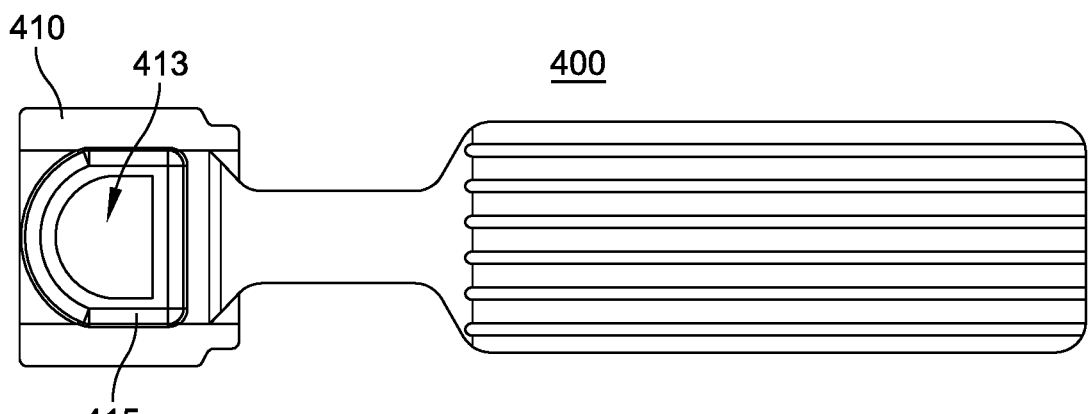
FIG. 7C is a top view of the interchangeable member shown in FIG. 7A.
Figure 7D:
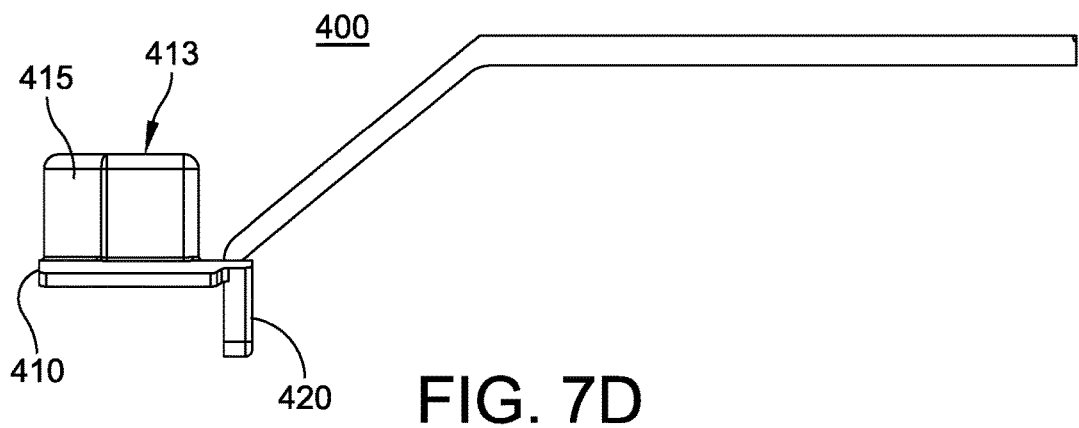
FIG. 7D is a side view of the interchangeable member shown in FIG. 7A.
Figure 7E:
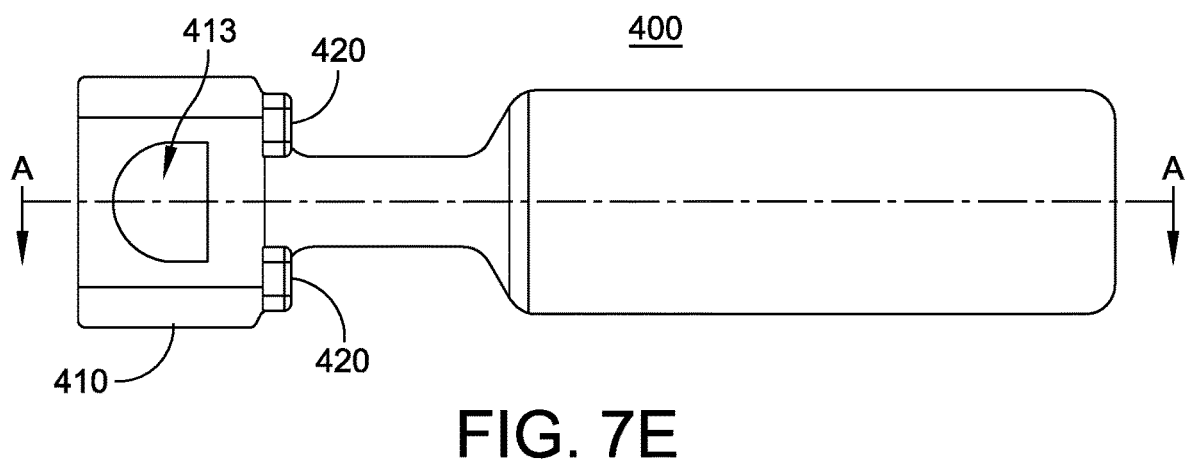
FIG. 7E is a bottom view of the interchangeable member shown in FIG. 7A.
Figure 7F:
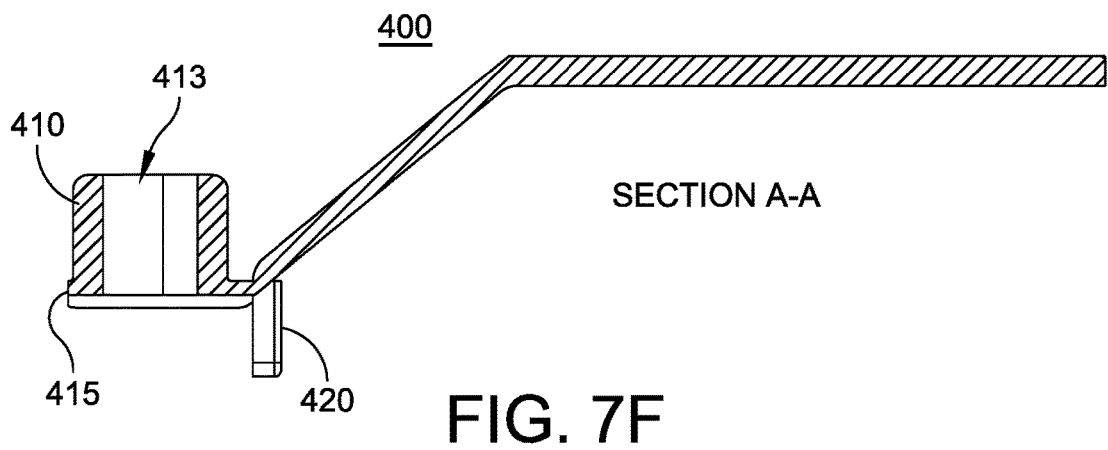
FIG. 7F is a cross-sectional view of the interchangeable member taken through the section line A-A shown in FIG. 7E.

As shown in FIGS. 7A and 7C, the cutting guide hole 413 has a half-cylinder shape to form a half-cylinder shaped cut into the bone surface. A different interchangeable members can be configured to have different cutting guide hole shape depending on the shape of the cut needed in the bone being shaped.

Figure 9A:
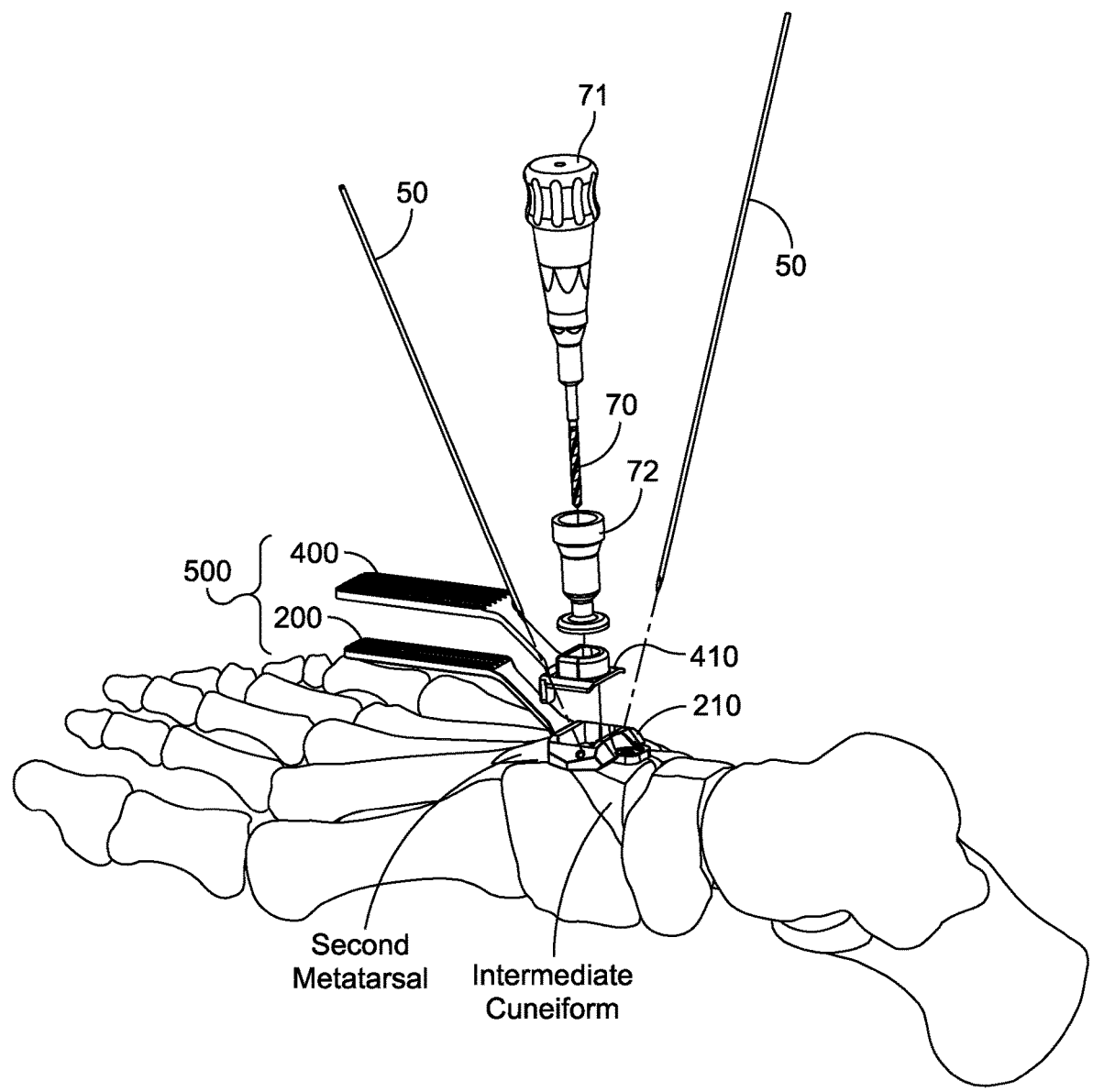

As shown in FIG. 9A, the interchangeable member 400 is assembled with the base member 200 to form a bone cutting guide assembly 500 by engaging the base member 200 from the top surface side of the base member 200. As shown in FIG. 6B, the main body 410 of the interchangeable member 400 can comprise two alignment tabs 420 for assisting the engagement of the interchangeable member 300 to the base member 200.

In some embodiments, each of the base member 200 and the interchangeable members 300, 400 further comprise a handle piece 230, 330, and 430, respectively. The handle piece 230, 330, 430 extends from their respective main body 210, 310, 410. The handle piece 230 of the base member and the handle piece 330, 430 of the interchangeable member 300, 400 overlap with one another when they are engaged so that a user can grip the overlapped handles to manipulate the cutting guide assembly 500.

Figure 8B:
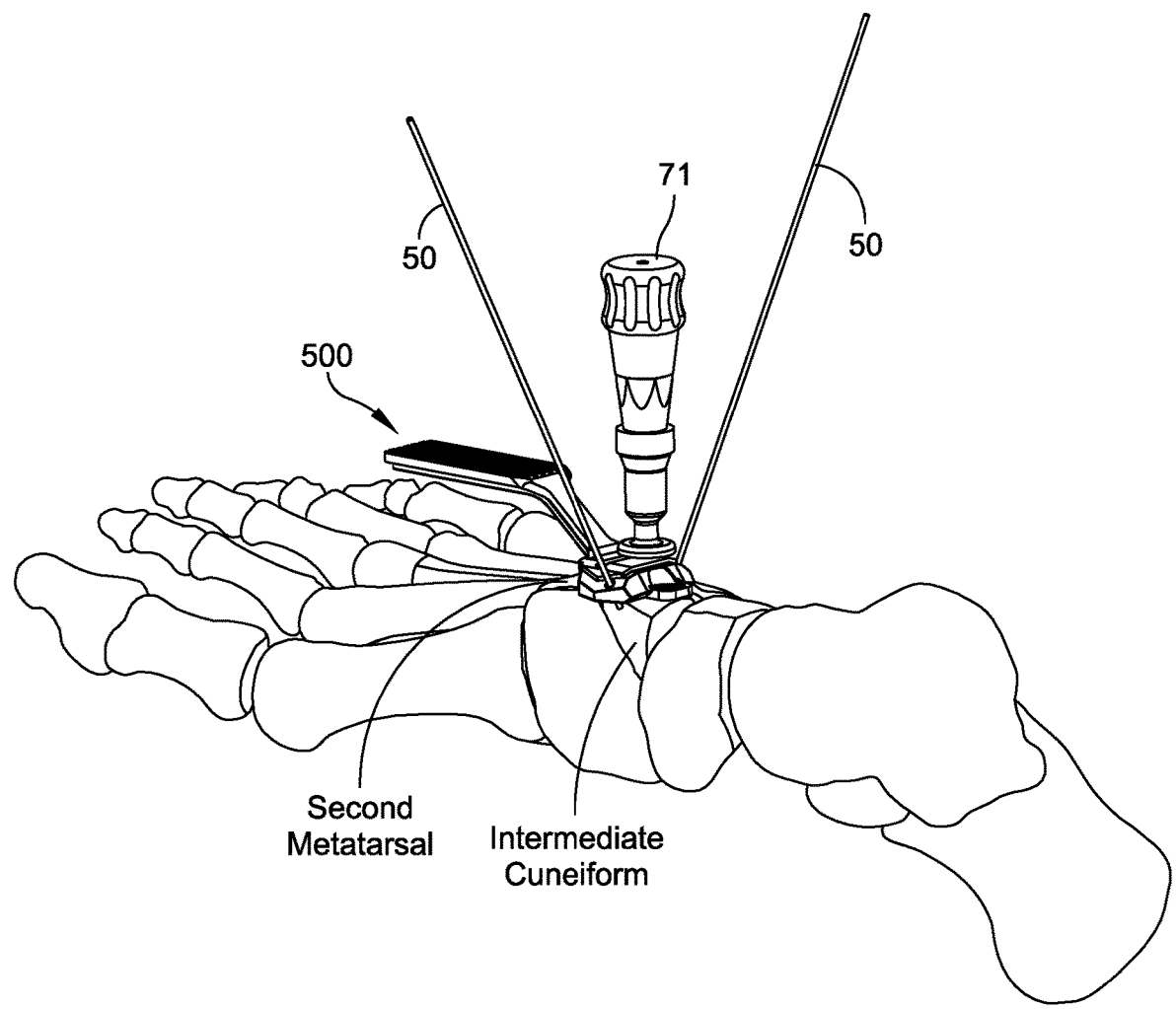
Figure 8C:
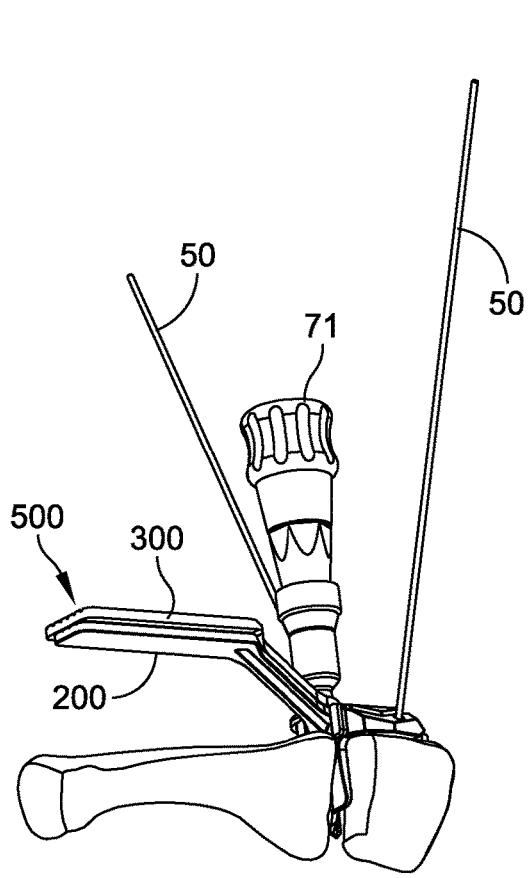
Figure 8D:
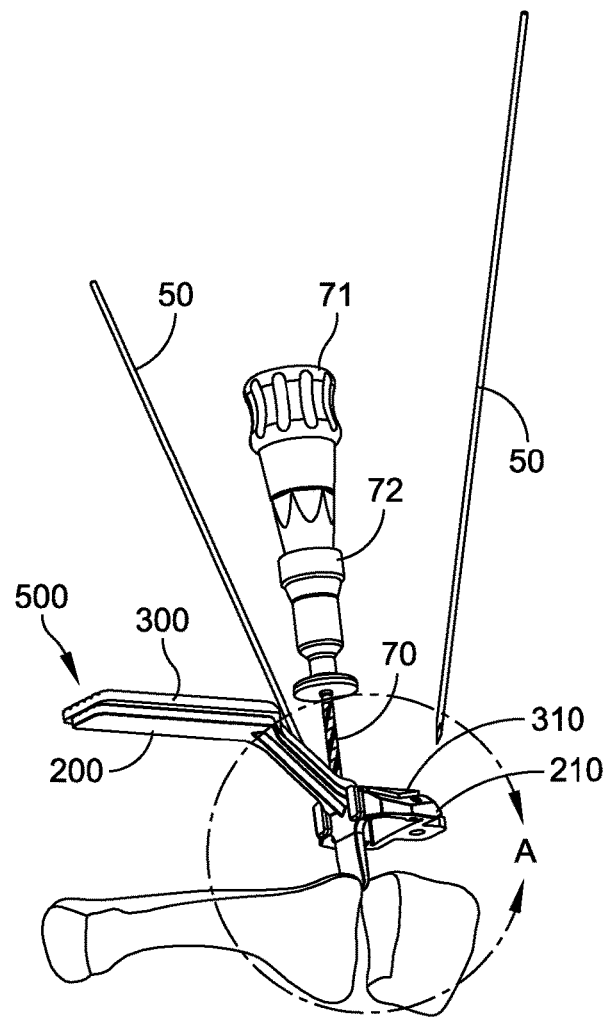
Figure 8E:
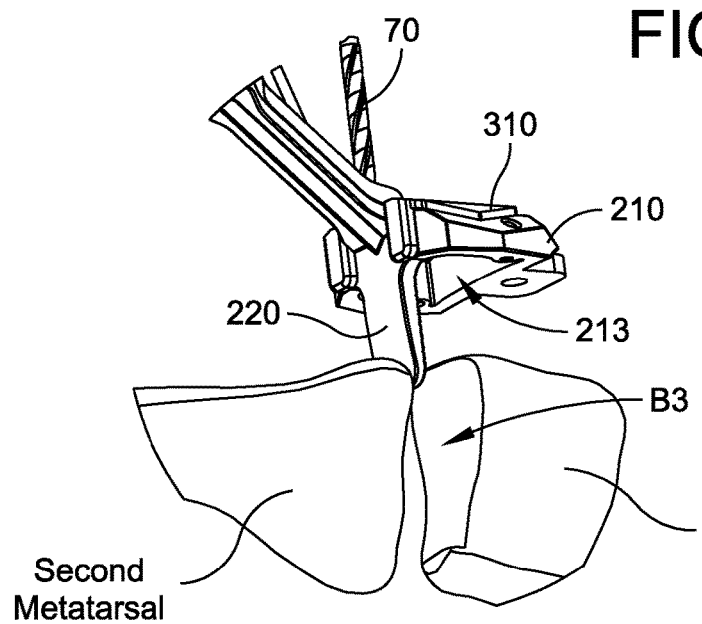

FIGS. 8A-8E are illustrations showing the use of the base member 200 and the interchangeable member 300 to form a cutting guide assembly 500 for making a flat cut bone surface B3 in a joint removing a cartilage surface to be repaired. After the base member 200 is positioned in a joint space by inserting the distractor tab 220, two guide wires 50 can be used to secure the main body 210 of the base member 200 to the bone. Then, the interchangeable member 300 is piggy backed on to the base member 200 as shown in FIG. 8A. FIGS. 8B-8C show using the bone cutting burr 70 to cut into the bone (the intermediate cuneiform bone in this example). After the bone cutting guide and the bone cutting burr 70 are removed, FIG. 8E show the flat resected bone surface B3.

Figure 9B:
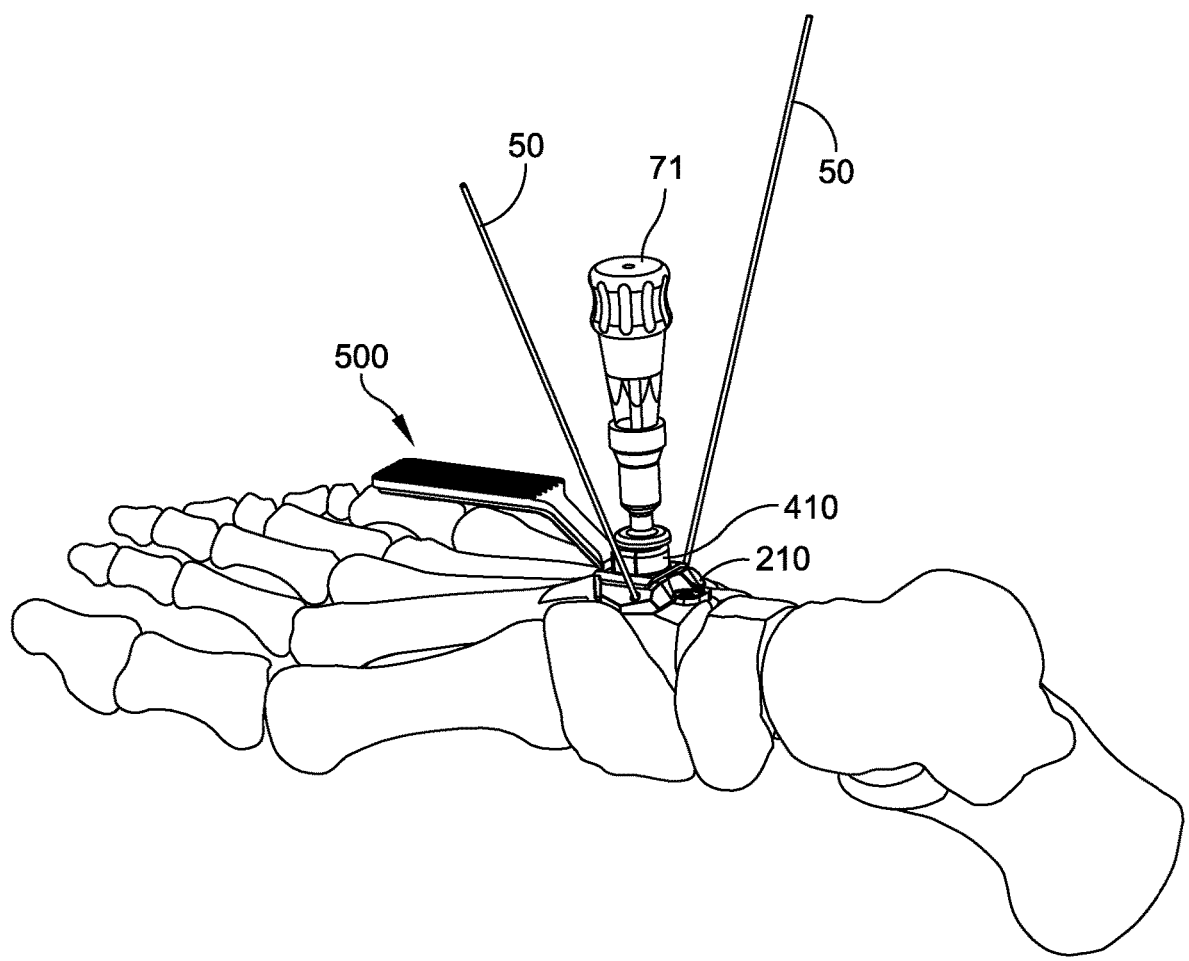
Figure 9C:
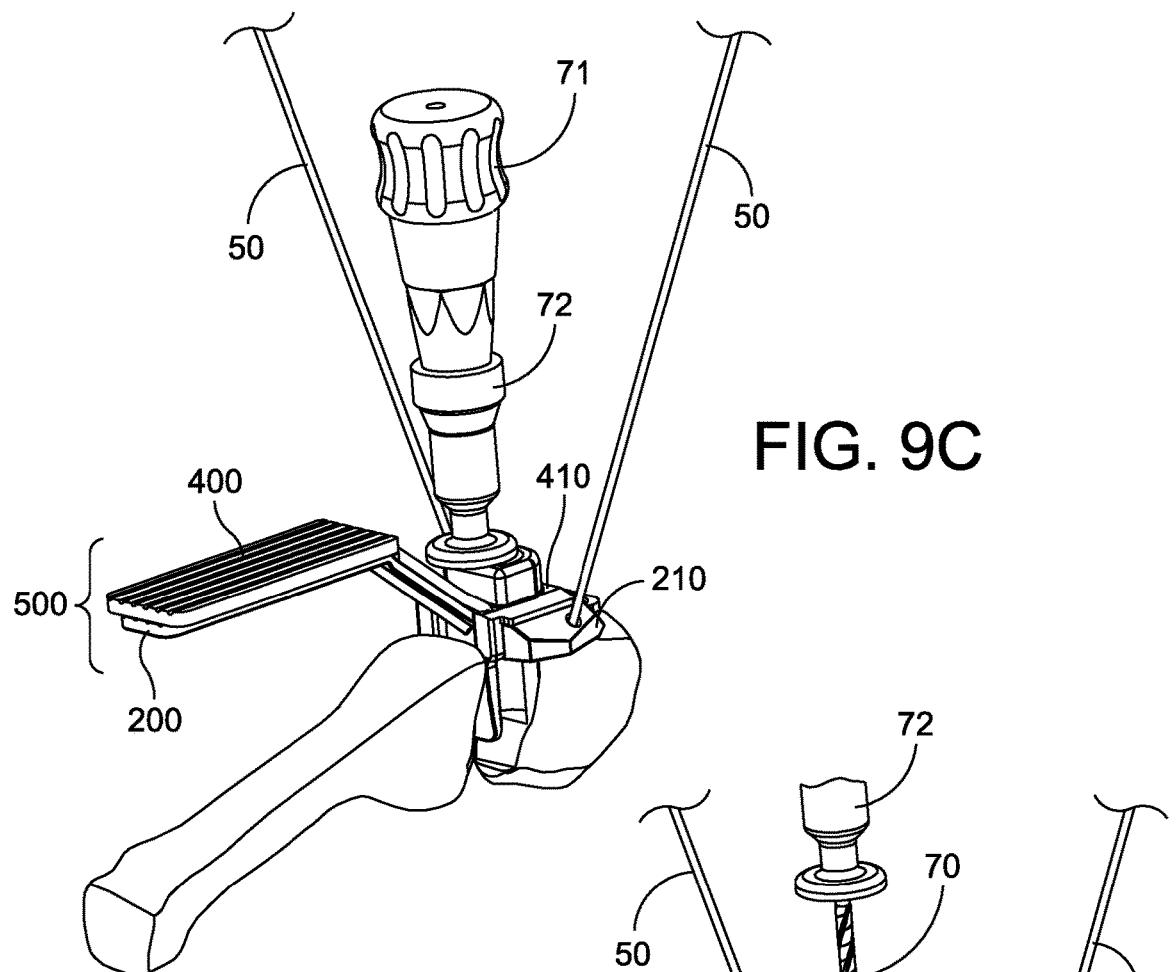
Figure 9D:
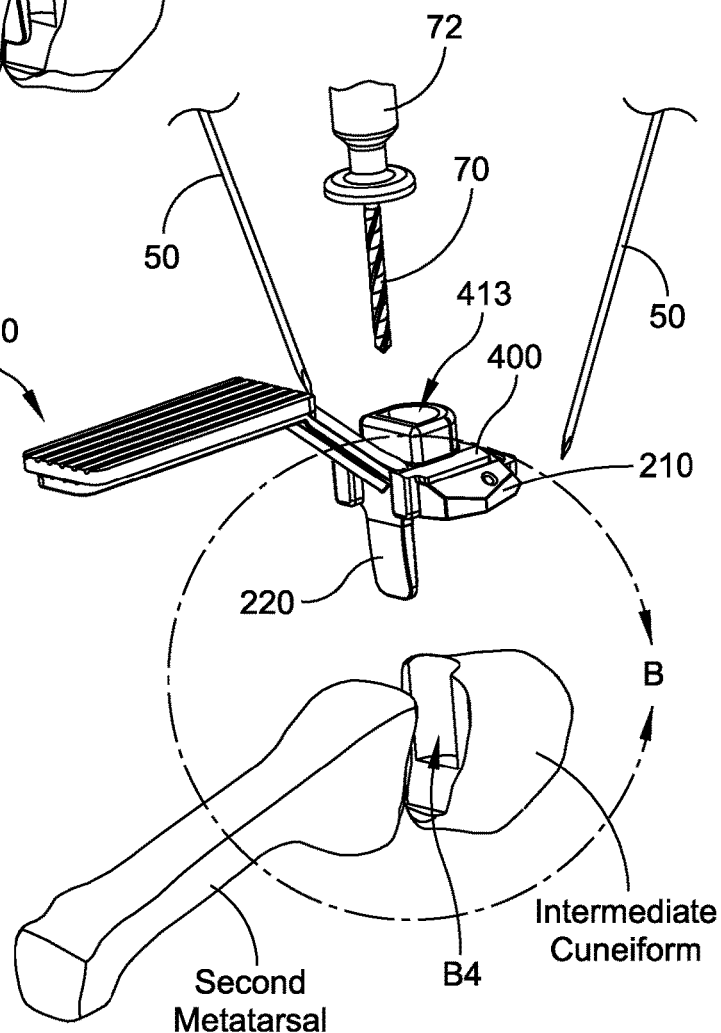

FIGS. 9A-9D are illustrations showing the use of the base member 200 and the interchangeable member 400 to form a cutting guide assembly 500 for making a half-cylinder cut bone surface B4 into the flat resected bone surface formed with using the interchangeable member 300 described above. After making the flat cut discussed above and removing the interchangeable member 300 from the base member 200, the base member 200 can be left in position in the joint space by inserting the distractor tab 220, the interchangeable member 400 is piggy backed on to the base member 200 as shown in FIG. 9A. FIGS. 9B-9C show using the bone cutting burr 70 to cut into the bone (the intermediate cuneiform bone in this example). After the bone cutting guide and the bone cutting burr 70 are removed, FIG. 9D show the half-cylinder cut bone surface B4 made into resected bone surface.

Figure 10A:
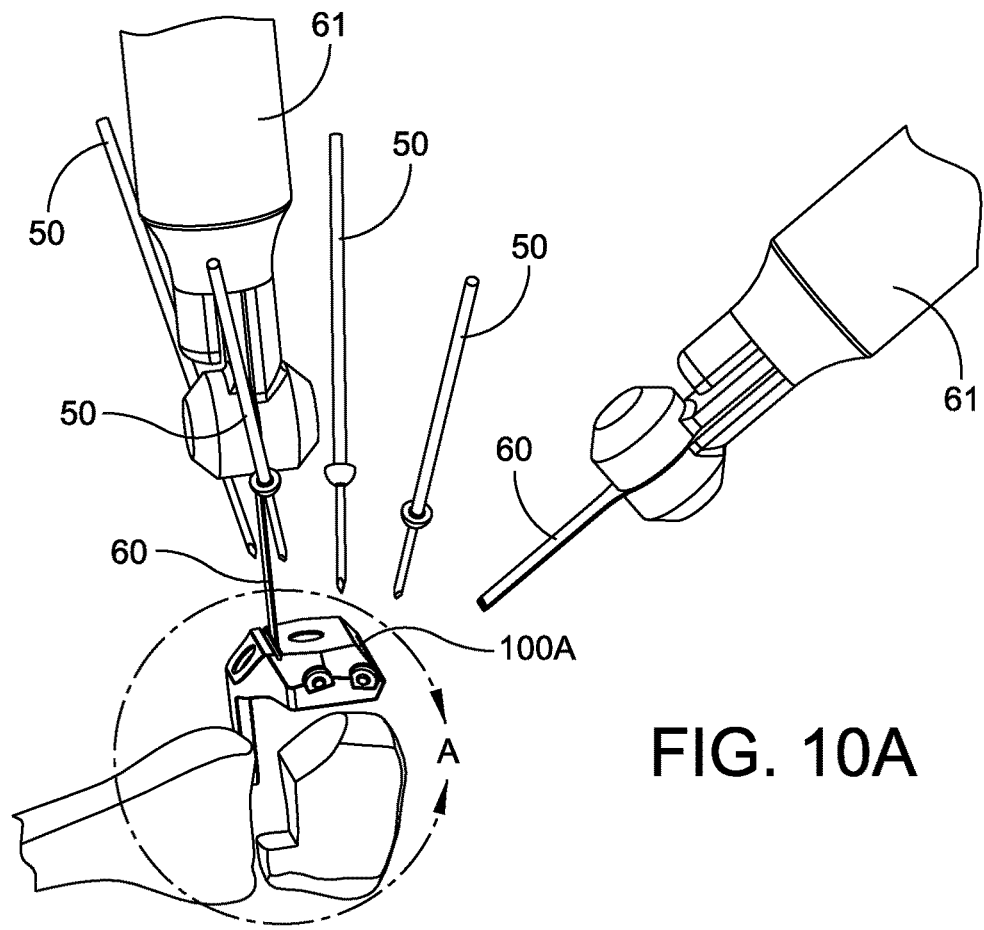
FIGS. 10A-10H are illustrations of the bone cutting guide embodiment in which the handle is configured to be removable from the guide's main body.
Figure 10B:
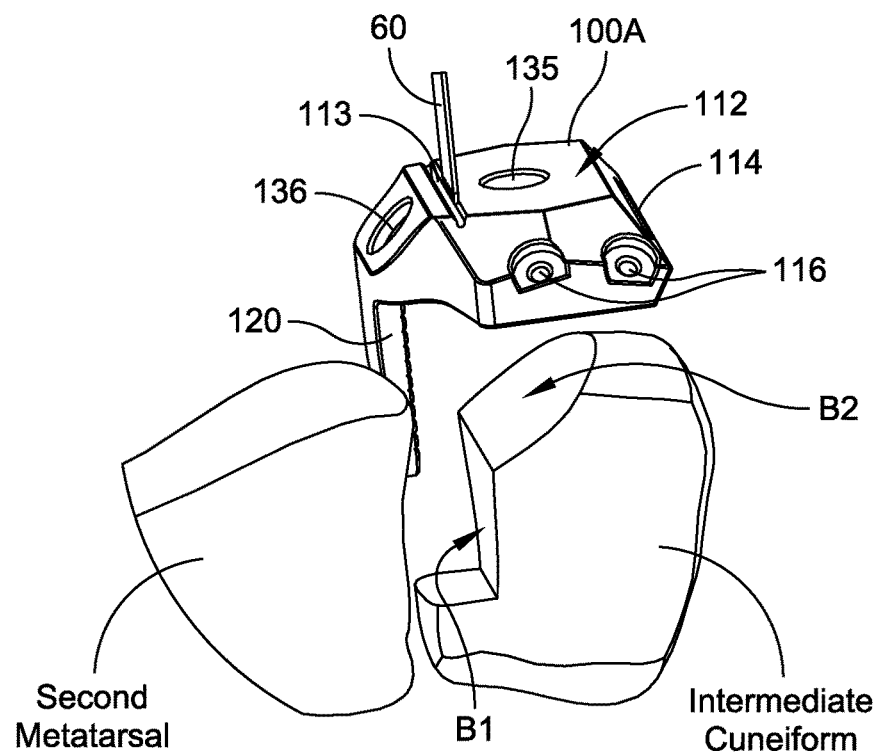

Referring to FIGS. 10A-10H, an example of an embodiment of a bone cutting guide 100A in which its handle piece 135 is detachable from the cutting guide 100A. FIGS. 10A and 10B show an exploded view and a close up view, respectively, of a joint space between the intermediate cuneiform bone and the second metatarsal, the bone cutting guide 100A, two bone cutting saw blades 60, and guide wires 50. This example of the bone cutting guide 100A comprises four holes 116 for receiving guide wires 50. One of the two bone cutting saw blades 60 is shown in the orientation to make a straight cut through the first slot 113 in the cutting guide. The other of the two bone cutting saw blades 60 is shown in the orientation to make an angled cut through the second slot 114 in the cutting guide.

The bone cutting guide 100A comprises a distractor tab 120 as with the other cutting guide embodiments described herein. The cutting guide 100A does not have an integrally formed handle piece but the bone cutting guide 100A comprises two or more handle-receiving recesses 135, 136. The two or more handle-receiving recesses can be oriented in different directions whereby the handle 130A can be attached to the main body in different orientations as desired.

In this example, the first handle-receiving recess 135 is configured to receive the handle 130A in orthogonal orientation relative to the bone contacting bottom surface 111 of the cutting guide 100A. This orientation can be seen in FIG. 10F where the handle 130A is shown fully inserted into the first handle-receiving recess 135. The second handle-receiving recess 136 is configured to receive the handle 130A at a predetermined angle. This orientation can be seen in FIG. 10H where the handle 130A is shown fully inserted into the second handle receiving recess 136.

Although the illustrated example bone cutting guide 100A has two handle-receiving recesses 135, 136, some embodiments can have one handle-receiving recess or more than two if appropriate. At least one handle-receiving recess is desired.

Figure 10C:
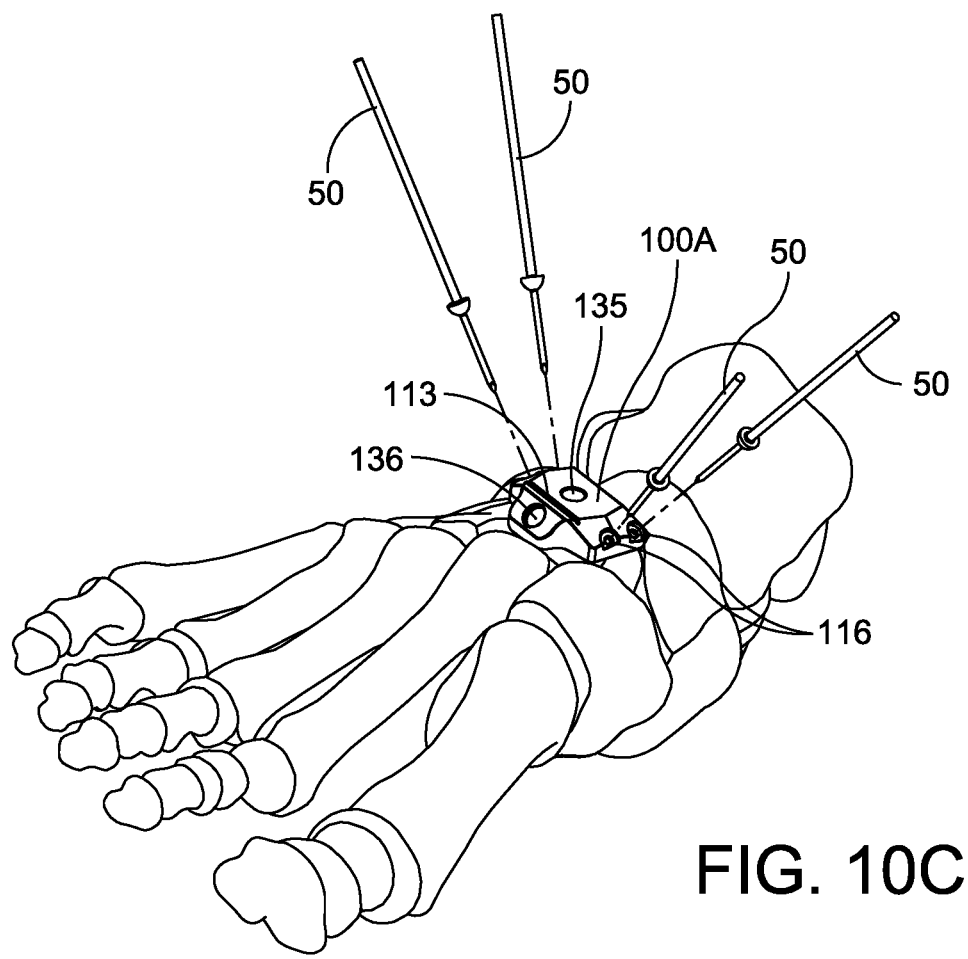
Figure 10D:
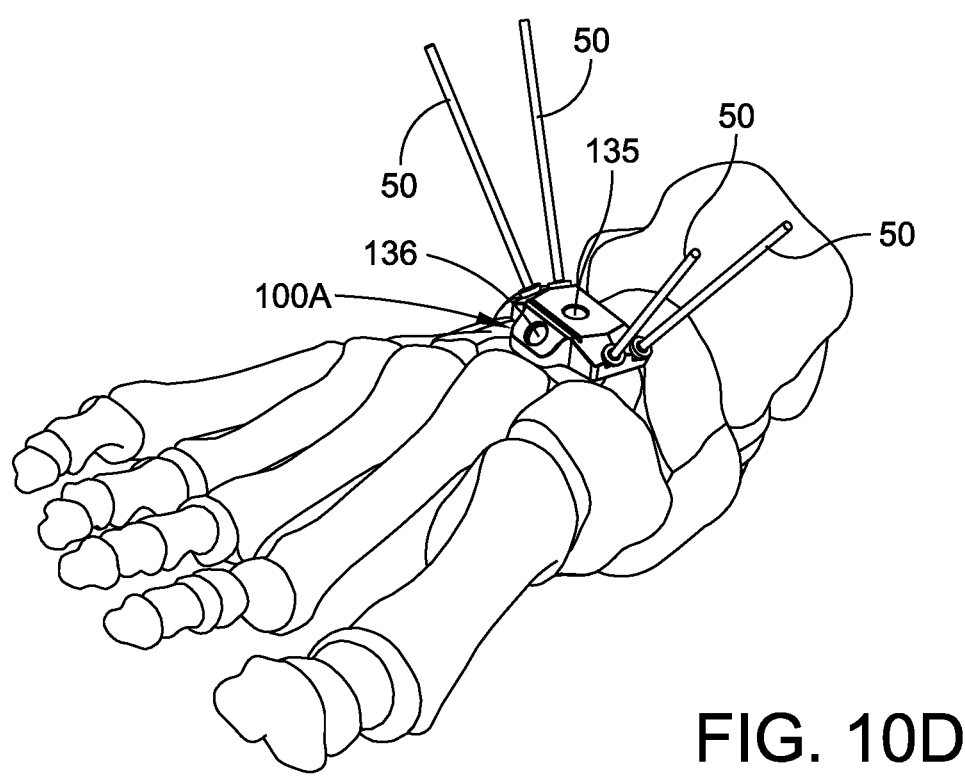
Figure 10E:
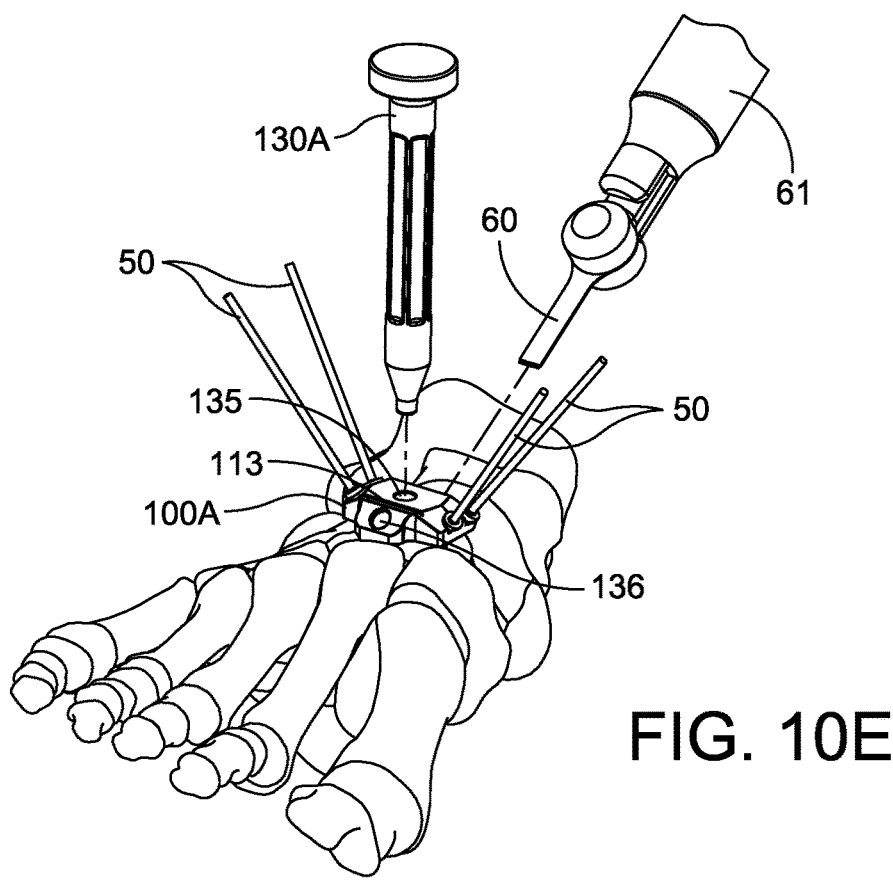
Figure 10F:
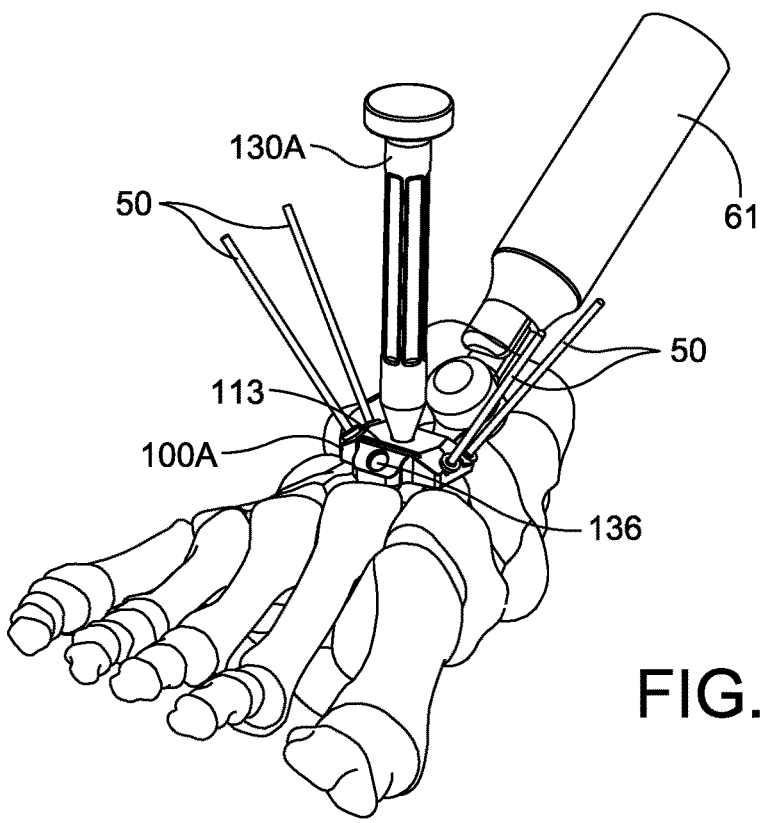

The removable handle 130A can be used in the orthogonal orientation shown in FIG. 10F to drive the distractor tab 120 into the joint space (either with manual force or by striking the handle with a mallet). A preferred sequence of using the bone cutting guide 100A to make two cuts in the bone (intermediate cuneiform in this example) to create the two angled resected bone surfaces B1 and B2 (see FIG. 19B) will now be described.

Referring to FIGS. 10C and 10D, after the bone cutting guide 100A is placed over the intended joint space and the distractor tab 120 is driven into the joint space, the cutting guide 100A is fixed in place with guide wires 50. In this example embodiment, the bone cutting guide 100A is provided with four holes 116, two on the medial side and two on the lateral side, to accommodate four guide wires 50.

Next, referring to FIGS. 10E and 10F, the removable handle 130A is attached to the bone cutting guide 100A by being inserted into the first handle-receiving recess 135. The handle 130A is used to hold the bone cutting guide 110A along with the patient's foot and the saw blade 60 is inserted into the angled second saw guide slot 114 to make the angled cut. The angled cut produces the second resected bone surface B2 shown in FIG. 10B.

Figure 10G:
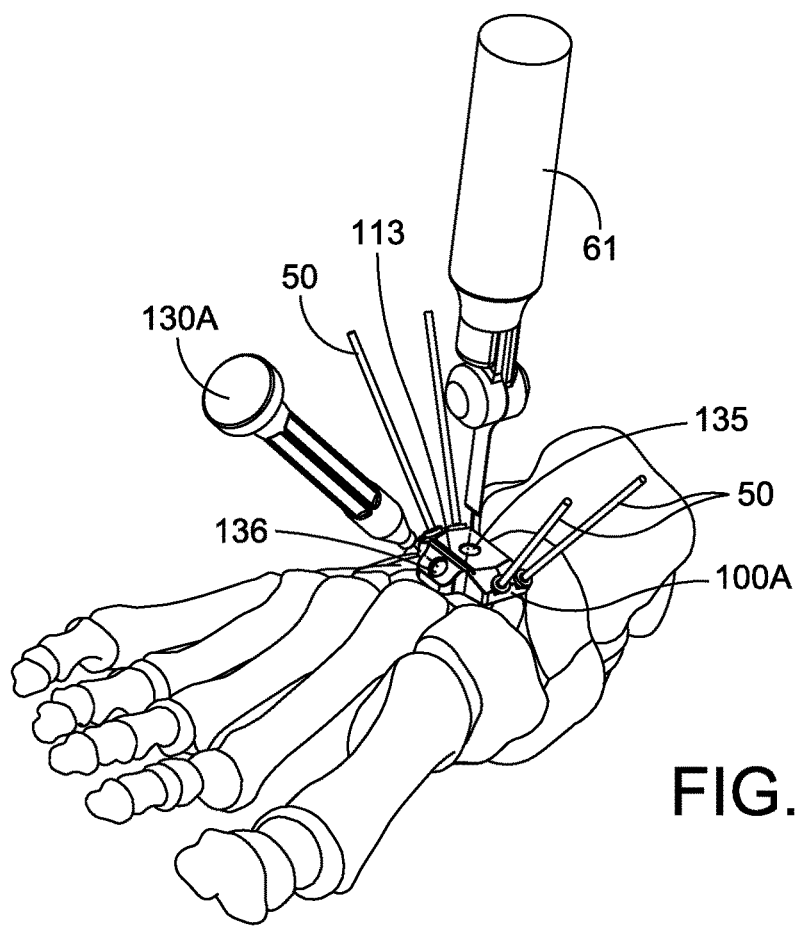
Figure 10H:
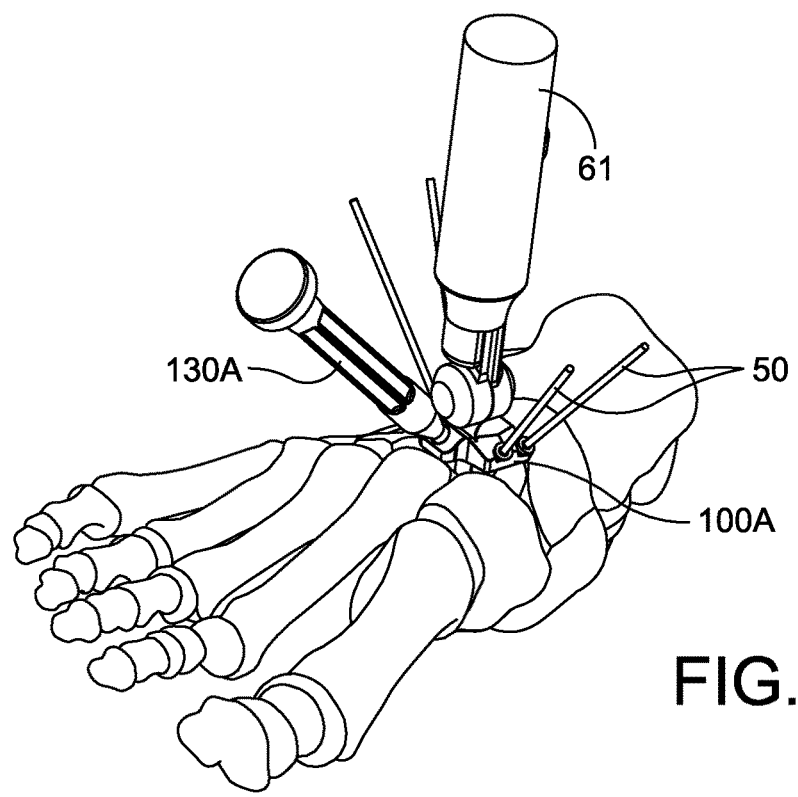

Next, referring to FIGS. 10G and 10H, the handle 130A is moved over to the second location by inserting it into the second handle-receiving hole 136. The second location for the handle 130A orients the handle 130A at an angle to allow the saw blade 60 to access the first saw guide slot 113. With the handle 130A attached to the bone cutting guide 100A in the angled orientation, the handle is used to hold the bone cutting guide 100A along with the patient's foot and the saw blade 60 is inserted into the vertically oriented first guide slot 113. The first saw guide slot 113 guides the saw blade 60 vertically down to the bone in a perpendicular orientation to the bone contacting bottom surface 111 of the bone cutting guide 100A. This allows the blade 60 to make the vertical (straight) cut that produces the first resected bone surface B1 shown in FIG. 10B. Additionally, when attached to the bone cutting guide 100A, the handle can also be used to apply pressure to the bone cutting guide 100A and provide additional stability while cutting the bone. In other words, using the handle, the surgeon can apply pressure to the bone cutting guide 100A and brace against the sawing motion of the sawing blade 60.

Figure 11:
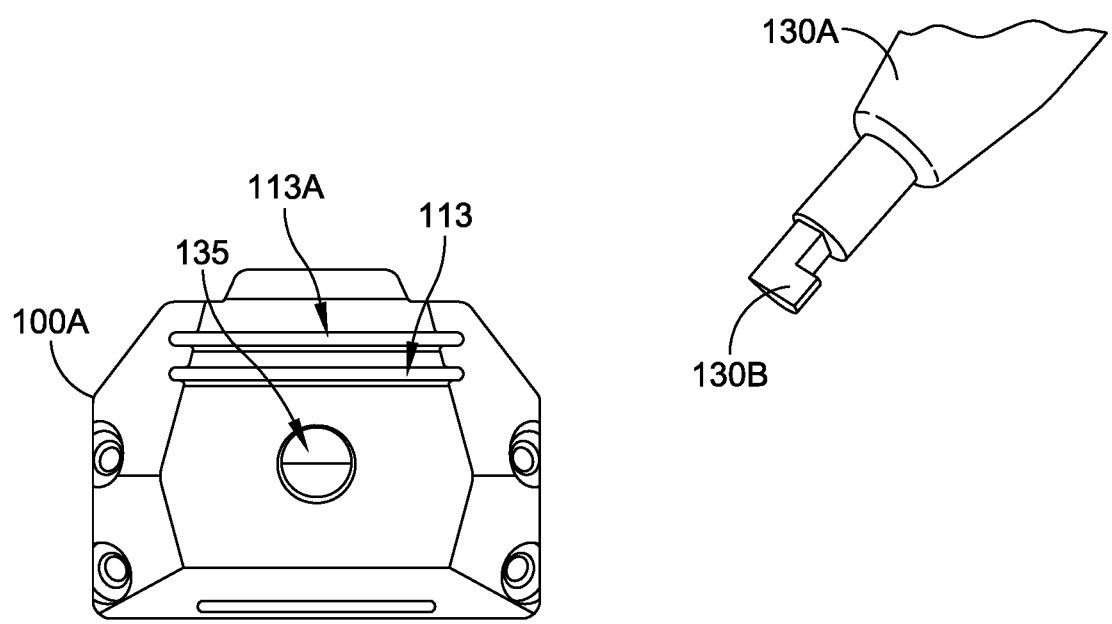
FIG. 11 is an illustration of another embodiment of the cutting guide and the accompanying removable handle.

Referring to FIG. 11, in some embodiments, the handle 130A and the handle-receiving recesses 135, 136 can be configured to be able to lock the handle 130A to the cutting guide 100A. For example, the portion of the cutting guide handle 130A that is inserted into the handle-receiving recess can comprise a male locking structure 130B while the handle-receiving recess 135, 136 can comprise a complimentary structure receiving the male locking structure. In some embodiments, the handle-receiving recess 135, 136 can be configured with a tab or a protrusion in the recess that interferes with the male locking structure 130B when the male locking structure 130B is at certain predetermined orientation. For example, after the male locking structure 130B is inserted into one of the handle receiving recesses 135 and 136, by turning the handle 130A a desired amount (e.g. quarter turn) will lock the cutting guide handle 130A to the cutting guide 100A. Other mechanical configuration that will allow locking and unlocking of the cutting guide handle 130A to the handle-receiving recess 135, 136 can be implemented.

The attached or removable handle 130A could also be oriented vertically such that a tamp or hammer could be used against the end of the handle to help drive the distractor tab into the joint space. A removable handle could have multiple attachment positions to allow force to be applied in different directions when driving the distractor tab into the joint. The attached or removable handle could be used to make adjustments to the position of the guide (in a joystick motion, for instance) while it is being inserted into the joint or after it has been inserted into the joint.

In some embodiments, the cutting guide 100A can comprise more than one vertically oriented saw guide slot 113. FIG. 11 also illustrates this embodiment. The cutting guide 100A in FIG. 11 is provided with a second vertically oriented saw guide slot 113A that is parallel with the first vertically oriented saw guide slot 113. The provision of the second vertically oriented saw guide slot 113A provides additional option for the placement of the vertical cut. Additionally, the extra vertically oriented saw guide slot 113' allows for easier cleanup with osteotome after cutting guide is removed.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

The invention claimed is:

1. A bone cutting guide assembly comprising:
    a base member comprising a main body, a bottom surface, a top surface, and a main opening, wherein the bottom surface is a bone contacting surface;
    a plurality of interchangeable members, wherein each interchangeable member comprises a main body that includes a bottom surface, and a cutting guide hole that extends through the interchangeable member, wherein the cutting guide hole on each interchangeable member has a different shape for guiding a bone cutting burr to make a different shaped cut in a bone, wherein the main body of each interchangeable member comprises an upper surface, a bottom surface, and a wall that extends upward from the upper surface to a predetermined height and defines the cutting guide hole, such that the wall stops a bone cutting burr from extending beyond a desired depth into the cutting guide hole, wherein the wall on each interchangeable member has a different height, wherein each interchangeable member is configured to engage the base member one at a time from the top surface of the base member, whereby the cutting guide hole overlaps with the main opening when the interchangeable member is engaged to the base member; and a distractor tab extending from the bottom surface of the main body.

2. The bone cutting guide assembly of claim 1, wherein the distractor tab is oriented perpendicular to the bottom surface and comprises a cartilage contacting surface configured for contacting a cartilage surface in the joint.

3. The bone cutting guide assembly of claim 2, wherein the cartilage contacting surface is textured to prevent slippage against the cartilage.

4. The bone cutting guide assembly of claim 2, wherein the bone contacting surface and the cartilage contacting surface are perpendicular to each other.

5. The bone cutting guide assembly of claim 1, wherein the main body further comprises at least two holes positioned for receiving guide wires for securing the main body to a bone.

6. The bone cutting guide assembly of claim 1, wherein the cutting guide hole has a width sufficient for guiding a bone cutting burr.

7. The bone cutting guide assembly of claim 1, further comprising a handle piece extending from the main body of the base member and a handle piece extending from the main body of each of the interchangeable member, wherein when the base member and one of the interchangeable member are engaged, the handle piece of the base member and the handle piece of the engaged interchangeable member overlap with one another so that a user can grip the overlapped handles to manipulate the cutting guide assembly.

8. The bone cutting guide assembly of claim 1, wherein the cutting guide hole in one of the plurality of interchangeable members has a straight elongated shape for forming a straight cut into the bone.

9. The bone cutting guide assembly of claim 1, wherein the cutting guide hole in one of the plurality of interchangeable members has a half-cylinder shape for forming a half-cylinder shaped cut into the bone.

10. The bone cutting guide assembly of claim 1, further comprising a pair of alignment tabs extending from the bottom surface of the interchangeable member's main body for assisting the engagement of the interchangeable member to the base member.

\* \* \* \* \*